United States Patent
Zakay-Rones et al.

(10) Patent No.: US 7,223,389 B2
(45) Date of Patent: May 29, 2007

(54) COMPOSITIONS AND METHODS FOR TREATMENT OF CANCER

(75) Inventors: Zichria Zakay-Rones, Jerusalem (IL); Amos Panet, Mevaseret Zion (IL); Charles Irving, Caeseria (IL)

(73) Assignees: Yissum Research Development Company of the Hebrew University of Jerusalem, Jerusalem (IL); Theravir Management L.P., Jerusalem (IL)

( * ) Notice: Subject to any disclaimer, the term of this patent is extended or adjusted under 35 U.S.C. 154(b) by 0 days.

(21) Appl. No.: 10/800,256

(22) Filed: Mar. 11, 2004

(65) Prior Publication Data
US 2005/0031642 A1  Feb. 10, 2005

Related U.S. Application Data

(63) Continuation of application No. PCT/IL02/00765, filed on Sep. 12, 2002.

(30) Foreign Application Priority Data
Sep. 12, 2001  (IL)  ...................... 145397

(51) Int. Cl.
*A61K 48/00* (2006.01)
*A01N 63/00* (2006.01)
(52) U.S. Cl. .................................... 424/93.2
(58) Field of Classification Search ................ 424/93.2
See application file for complete search history.

(56) References Cited

U.S. PATENT DOCUMENTS

| | | | |
|---|---|---|---|
| 5,118,502 A | 6/1992 | Glisson et al. | |
| 5,602,023 A | 2/1997 | Csatary | |
| 5,733,556 A * | 3/1998 | Schrier et al. | 424/214.1 |
| 5,762,938 A * | 6/1998 | Paoletti et al. | 424/199.1 |
| 6,464,984 B2 | 10/2002 | Audonnet et al. | |
| 6,719,979 B2 * | 4/2004 | Peeters et al. | 424/214.1 |
| 7,056,689 B1 | 6/2006 | Lorence et al. | 435/7.23 |
| 2003/0044384 A1 | 3/2003 | Roberts et al. | |
| 2003/0077819 A1 * | 4/2003 | Groene et al. | 435/325 |

OTHER PUBLICATIONS

U.S. Appl. No. 60/290,051.*
David Tzadok et al., "The effect of a mesogenic and a lentogenic newcastle disease virus strain on burkitt lymphoma daudi cells" J. Cancer Res. Clin. Oncol. 1995, vol. 121, pp. 169-174 (1995).
Schirrmacher et al. "Antitumor effects of newcastle disease virus in vivo: local versus systemic effects" International Journal of Oncology 2001, vol. 18, pp. 945-952 (2001).
Phuangsab et al., "Newcastle disease virus therapy of human tumor xenografts: Antitumor effects of local or systemic administration," *Cancer Ltrs.*, 172: 27-36 (Oct. 2001).
Freeman et al., "Phase I/II trial of intravenous NDV-HUJ oncolytic virus in recurrent glioblastoma multiforme," *Molecular Therapy*, pp. 1-8 (Nov. 2005).

* cited by examiner

*Primary Examiner*—Brian Whiteman
(74) *Attorney, Agent, or Firm*—Winston & Strawn LLP

(57) ABSTRACT

The present invention discloses lentogenic viral strains useful in the treatment of cancer. A preferred viral strain of Newcastle Disease Virus (NDV) is specifically characterized in terms of biological activities. The present invention further discloses treatment of cancer by application of a clonal NDV strain to tumors. Another feature of the invention is the use of at least one isolated viral glycoprotein or a subunit or analog thereof or of an isolated polynucleotide encoding the same for the treatment of cancer.

10 Claims, 13 Drawing Sheets

```
   1  MGSRPSTKNP  APMMLTIRVA  LALSCICPAN  SIDGRPLAAA  GIVVTGDKAV
  51  NIYTSSQTGS  IIVKLLPNLP  KDKEACAKAP  LDAYNRTLTT  LLTPLGDSIR
 101  RIQESVTTSG  GGRQGRLIGA  IIGGVALGVA  TAAQITAAAA  LIQAKQNAAN
 151  ILRLKESIAA  TNEAVHEVTD  GLSQLAVAVG  KMQQFVNDQF  NKTAQELDCI
 201  KIAQQVGVEL  NLYLTELTTV  FGPQITSPAL  NKLTIQALYN  LAGGNMDYLL
 251  TKLGVGNNQL  SSLIGSGLIT  GNPILYDSQT  QLLGIQVTLP  SVGNLNNMRA
 301  TYLETLSVST  TRGFASALVP  KVVTQVGSVI  EELDTSYCIE  TDLDLYCTRI
 351  VTFPMSPGIY  SCLSGNTSAC  MYSKTEGALT  TPYMTIKGSV  IANCKMTTCR
 401  CVNPPGIISQ  NYGEAVSLID  KQSCNVLSLG  GITLRLSGEF  DVTYQKNISI
 451  QDSQVIITGN  LDISTELGNV  NNSISNALNK  LEESNRKLDK  VNVKLTSTSA
 501  LITYIVLTII  SLVFGILSLI  LACYLMYKQK  AQQKTLLWLG  NNTLDQMRAT
 551  TKM*TQMRNE  GFPNSNLCES  SGSLSVQRVK  KKLPVVDDQR  TIYG*NGKRG
 601  RPSIASQASQ  PPFYRFTDNS  PQSWTAPLAK  LR*RMMKERQ  KIHGA*YSGL
 651  QSYS*Q**PW  LYL*PPFYIA  WGLAHLAIL*  AYRLGFPGQK  KRLHLHLVPI
 701  KM**IGYISK  WPLSLRWHC*  ILRPQL*TQ*  HLSLIRLMEL  QTTVGGGHLS
 751  MTQII*GG*A  KNSL*MMLVM  SHHSIPLHFK  NI*ILSRRLL  QDQVALEYPH
 801  LT*VLPITAT  PIM*YCLDAE  ITHIHISI*H  LVCSGHLQQG  GYSFLLCVPS
 851  TWTTPKIGSL  AV*VQLPWVV  ICCARKSRRQ  RKKIITQLSL  RGWYMGG*GS
 901  TASTTKRT*M  SQHYSGTWP   TTQE*GVDLL  LTAAYGSQST  EG*NPIHPVT
 951  LYRKGNM*YT  SDTMTHAQMS  KTTRFEWPSL  RISLDGLVGN  AYSRLSYLSR
1001  CQHP*AKTRY  *LYRPTQSHS  WGPKAEFSQ*  GHLISCINEG  HHTSLPRYYI
1051  L*QSATKQPL  FIVLIHSMPS  LGQVVSLARL  QQDAPTRVLL  ESIQIHIP*S
1101  SIET
```

SEQ ID NO. 2

FIGURE 10

SEQUENCE LISTING

```
<160> NUMBER OF SEQ ID NOS: 35

<210> SEQ ID NO 1
<211> LENGTH: 3358
<212> TYPE: DNA
<213> ORGANISM: Newcastle disease virus

<400> SEQUENCE: 1
acgggtagaa gattctggat cccggttggc gccctccagg tgcaagatgg gctccagacc     60
ttctaccaag aacccagcac ctatgatgct gactatccgg gttgcgctgg cactgagttg    120
catctgtccg gcaaactcca ttgatggcag gcctcttgca gctgcaggaa ttgtggttac    180
aggagacaaa gccgtcaaca tatacacctc atcccagaca ggatcaatca tagttaagct    240
cctcccgaat ctgcccaagg ataaggaggc atgtgcgaaa gcccccttgg atgcatacaa    300
caggacattg accactttgc tcacccccct tggtgactct atccgtagga tacaagagtc    360
tgtgactaca tctggagggg ggagacaggg gcgccttata ggcgccatta ttggcggtgt    420
ggctcttggg gttgcaactg ccgcacaaat aacagcggcc gcagctctga tacaagccaa    480
acaaaatgct gccaacatcc tccgacttaa agagagcatt gccgcaacca atgaggctgt    540
gcatgaggtc actgacggat tatcgcaact agcagtggca gttgggaaga tgcagcagtt    600
tgttaatgac caatttaata aaacagctca ggaattagac tgcatcaaaa ttgcacagca    660
agttggtgta gagctcaacc tgtacctaac cgaattgact acagtattcg gaccacaaat    720
cacttcacct gctttaaaca agctgactat tcaggcactt tacaatctag ctggtggaaa    780
tatggattac ttattgacta gttaggtgt agggaacaat caactcagct cattaatcgg    840
tagcggctta atcaccggta accctattct atacgactca cagactcaac tcttgggtat    900
acaggtaact ctaccttcag tcgggaacct aaataatatg cgtgccacct acttggaaac    960
```

```
cttatccgta agcacaacca ggggatttgc ctcggcactt gtcccaaaag tggtgacaca    1020
ggtcggttct gtgatagaag aacttgacac ctcatactgt atagaaactg acttagattt    1080
atattgtaca agaatagtaa cgttccctat gtcccctggt atttattcct gcttgagcgg    1140
caatacgtcg gcctgtatgt actcaaagac cgaaggcgca cttactacac catacatgac    1200
tatcaaaggt tcagtcatcg ccaactgcaa gatgacaaca tgtagatgtg taaaccccccc   1260 gggtatcata tcgcaaaact atggagaagc cgtgtctcta atagataaac aatcatgcaa    1320
tgttttatcc ttaggcggga taactttaag gctcagtggg gaattcgatg taacttatca    1380
gaagaatatc tcaatacaag attctcaagt aataataaca ggcaatcttg atatctcaac    1440
tgagcttggg aatgtcaaca actcgatcag taatgctttg aataagttag aggaaagcaa    1500
cagaaaacta gacaaagtca atgtcaaact gactagcaca tctgctctca ttacctatat    1560
cgttttgact atcatatctc ttgttttttgg tatacttagc ctgattctag catgctacct    1620
aatgtacaag caaaagcgc aacaaaaaac cttattatgg cttgggaata atactctaga    1680
tcagatgaga gccactacaa aaatgtgaac acagatgagg aacgaaggtt tccctaatag    1740
taatttgtgt gaaagttctg gtagtctgtc agttcagaga gttaagaaaa aactaccggt    1800
tgtagatgac caaggacga tatacgggta gaacggtaag agaggccgcc cctcaattgc     1860
gagccaggct tcacaacctc cgttctaccg cttcaccgac aacagtcctc aatcatggac    1920
cgcgccgtta gccaagttgc gttagagaat gatgaaagag aggcaaaaaa tacatggcgc    1980
ttgatattcc ggattgcaat cttattctta acagtagtga ccttggctat atctgtagcc    2040
tcccttttat atagcatggg ggctagcaca cctagcgatc ttgtaggcat accgactagg    2100
atttccaggg cagaagaaaa gattacatct acacttggtt ccaatcaaga tgtagtagat    2160
aggatatata agcaagtggc ccttgagtct ccgttggcat tgttaaatac tgagaccaca    2220
attatgaacg caataacatc tctctcttat cagattaatg gagctgcaaa caacagtggg    2280 tgggggcac ctatccatga cccagattat atagggggga taggcaaaga actcattgta     2340
gatgatgcta gtgatgtcac atcattctat ccctctgcat ttcaagaaca tctgaatttt    2400
atcccggcgc ctactacagg atcaggttgc actcgaatac cctcatttga catgagtgct    2460
acccattact gctacaccca taatgtaata ttgtctggat gcagagatca ctcacattca    2520
tatcagtatt tagcacttgg tgtgctccgg acatctgcaa cagggagggt attcttttct    2580
actctgcgtt ccatcaacct ggacgacacc caaaatcgga agtcttgcag tgtgagtgca    2640
actcccctgg gttgtgatat gctgtgctcg aaagtcacgg agacagagga agaagattat    2700
aactcagctg tccctacgcg gatggtacat gggaggttag ggttcgacgg ccagtaccac    2760
gaaaaggacc tagatgtcac aacattattc ggggactggg tggccaacta cccaggagta    2820 ggggggtggat cttttattga cagccgcgta tggttctcag tctacggagg gttaaaaccc    2880
aattcaccca gtgacactgt acaggaaggg aaatatgtga tatacaagcg atacaatgac    2940
acatgcccag atgagcaaga ctaccagatt cgaatggcca agtcttcgta taagcctgga    3000
cggtttggtg ggaaacgcat acagcaggct atcttatcta tcaaggtgtc aacatcctta    3060
ggcgaagacc cggtactgac tgtaccgccc aacacagtca cactcatggg ggccgaaggc    3120
agaattctca cagtagggac atctcatttc ttgtatcaac gagggtcatc atacttctct    3180
cccgcgttat tatatcctat gacagtcagc aacaaaacag ccactcttca tagtccttat    3240
acattcaatg cctcactcg gccaggtagt atcccttgcc aggcttcagc aagatgcccc    3300
aactcgtgtg ttactggagt ctatacagat ccatatcccc taatcttcta tagaaacc     3358
```

-continued

<210> SEQ ID NO 2
<211> LENGTH: 553
<212> TYPE: PRT
<213> ORGANISM: Newcastle disease virus

<400> SEQUENCE: 2

Met Gly Ser Arg Pro Ser Thr Lys Asn Pro Ala Pro Met Met Leu Thr
1 5 10 15

Ile Arg Val Ala Leu Ala Leu Ser Cys Ile Cys Pro Ala Asn Ser Ile
20 25 30

Asp Gly Arg Pro Leu Ala Ala Ala Gly Ile Val Val Thr Gly Asp Lys
35 40 45

Ala Val Asn Ile Tyr Thr Ser Ser Gln Thr Gly Ser Ile Ile Val Lys
50 55 60

Leu Leu Pro Asn Leu Pro Lys Asp Lys Glu Ala Cys Ala Lys Ala Pro
65 70 75 80

Leu Asp Ala Tyr Asn Arg Thr Leu Thr Thr Leu Leu Thr Pro Leu Gly
85 90 95

Asp Ser Ile Arg Arg Ile Gln Glu Ser Val Thr Thr Ser Gly Gly Gly
100 105 110

Arg Gln Gly Arg Leu Ile Gly Ala Ile Ile Gly Gly Val Ala Leu Gly
115 120 125

Val Ala Thr Ala Ala Gln Ile Thr Ala Ala Ala Ala Leu Ile Gln Ala
130 135 140

Lys Gln Asn Ala Ala Asn Ile Leu Arg Leu Lys Glu Ser Ile Ala Ala
145 150 155 160

Thr Asn Glu Ala Val His Glu Val Thr Asp Gly Leu Ser Gln Leu Ala
165 170 175

Val Ala Val Gly Lys Met Gln Gln Phe Val Asn Asp Gln Phe Asn Lys
180 185 190

Thr Ala Gln Glu Leu Asp Cys Ile Lys Ile Ala Gln Gln Val Gly Val
195 200 205

Glu Leu Asn Leu Tyr Leu Thr Glu Leu Thr Thr Val Phe Gly Pro Gln
210 215 220

Ile Thr Ser Pro Ala Leu Asn Lys Leu Thr Ile Gln Ala Leu Tyr Asn
225 230 235 240

Leu Ala Gly Gly Asn Met Asp Tyr Leu Leu Thr Lys Leu Gly Val Gly
245 250 255

Asn Asn Gln Leu Ser Ser Leu Ile Gly Ser Gly Leu Ile Thr Gly Asn
260 265 270

Pro Ile Leu Tyr Asp Ser Gln Thr Gln Leu Leu Gly Ile Gln Val Thr
275 280 285

Leu Pro Ser Val Gly Asn Leu Asn Asn Met Arg Ala Thr Tyr Leu Glu
290 295 300

Thr Leu Ser Val Ser Thr Thr Arg Gly Phe Ala Ser Ala Leu Val Pro
305 310 315 320

Lys Val Val Thr Gln Val Gly Ser Val Ile Glu Glu Leu Asp Thr Ser
325 330 335

Tyr Cys Ile Glu Thr Asp Leu Asp Leu Tyr Cys Thr Arg Ile Val Thr
340 345 350

Phe Pro Met Ser Pro Gly Ile Tyr Ser Cys Leu Ser Gly Asn Thr Ser
355 360 365

Ala Cys Met Tyr Ser Lys Thr Glu Gly Ala Leu Thr Thr Pro Tyr Met

-continued

```
              370                 375                 380
Thr Ile Lys Gly Ser Val Ile Ala Asn Cys Lys Met Thr Thr Cys Arg
385                 390                 395                 400

Cys Val Asn Pro Pro Gly Ile Ile Ser Gln Asn Tyr Gly Glu Ala Val
                405                 410                 415

Ser Leu Ile Asp Lys Gln Ser Cys Asn Val Leu Ser Leu Gly Gly Ile
                420                 425                 430

Thr Leu Arg Leu Ser Gly Glu Phe Asp Val Thr Tyr Gln Lys Asn Ile
                435                 440                 445

Ser Ile Gln Asp Ser Gln Val Ile Ile Thr Gly Asn Leu Asp Ile Ser
                450                 455                 460

Thr Glu Leu Gly Asn Val Asn Asn Ser Ile Ser Asn Ala Leu Asn Lys
465                 470                 475                 480

Leu Glu Glu Ser Asn Arg Lys Leu Asp Lys Val Asn Val Lys Leu Thr
                485                 490                 495

Ser Thr Ser Ala Leu Ile Thr Tyr Ile Val Leu Thr Ile Ile Ser Leu
                500                 505                 510

Val Phe Gly Ile Leu Ser Leu Ile Leu Ala Cys Tyr Leu Met Tyr Lys
                515                 520                 525

Gln Lys Ala Gln Gln Lys Thr Leu Leu Trp Leu Gly Asn Asn Thr Leu
                530                 535                 540

Asp Gln Met Arg Ala Thr Thr Lys Met
545                 550

<210> SEQ ID NO 3
<211> LENGTH: 21
<212> TYPE: DNA
<213> ORGANISM: Newcastle disease virus

<400> SEQUENCE: 3
tgaccacgag gttacctcta c                                          21

<210> SEQ ID NO 4
<211> LENGTH: 21
<212> TYPE: DNA
<213> ORGANISM: Newcastle disease virus

<400> SEQUENCE: 4
tccaagtagg tggcacgcat a                                          21

<210> SEQ ID NO 5
<211> LENGTH: 22
<212> TYPE: DNA
<213> ORGANISM: Newcastle disease virus

<400> SEQUENCE: 5
aattgactac agtattcgga cc                                         22

<210> SEQ ID NO 6
<211> LENGTH: 21
<212> TYPE: DNA
<213> ORGANISM: Newcastle disease virus

<400> SEQUENCE: 6
tgttgacatt cccaagctca g                                          21

<210> SEQ ID NO 7
<211> LENGTH: 20
<212> TYPE: DNA
```

```
<213> ORGANISM: Newcastle disease virus

<400> SEQUENCE: 7
gctcagtcat cgctaactgc                                              20

<210> SEQ ID NO 8
<211> LENGTH: 21
<212> TYPE: DNA
<213> ORGANISM: Newcastle disease virus

<400> SEQUENCE: 8
cggaatatca agcgccatgt a                                            21

<210> SEQ ID NO 9
<211> LENGTH: 21
<212> TYPE: DNA
<213> ORGANISM: Newcastle disease virus

<400> SEQUENCE: 9
ttagaaaaaa cacgggtaga a                                            21

<210> SEQ ID NO 10
<211> LENGTH: 21
<212> TYPE: DNA
<213> ORGANISM: Newcastle disease virus

<400> SEQUENCE: 10
acaggacatt gaccactttg c                                            21

<210> SEQ ID NO 11
<211> LENGTH: 22
<212> TYPE: DNA
<213> ORGANISM: Newcastle disease virus

<400> SEQUENCE: 11
caggtaactc taccttcagt cg                                           22

<210> SEQ ID NO 12
<211> LENGTH: 23
<212> TYPE: DNA
<213> ORGANISM: Newcastle disease virus

<400> SEQUENCE: 12
caactcgatc agtaatgctt tga                                          23

<210> SEQ ID NO 13
<211> LENGTH: 25
<212> TYPE: DNA
<213> ORGANISM: Newcastle disease virus

<400> SEQUENCE: 13
cctagatcag atgagagcca ctaca                                        25

<210> SEQ ID NO 14
<211> LENGTH: 20
<212> TYPE: DNA
<213> ORGANISM: Newcastle disease virus

<400> SEQUENCE: 14
ctgctgcatc ttcccaactg                                              20

<210> SEQ ID NO 15
<211> LENGTH: 23
```

```
<212> TYPE: DNA
<213> ORGANISM: Newcastle disease virus

<400> SEQUENCE: 15
gactcttgta tcctacggat aga                                    23

<210> SEQ ID NO 16
<211> LENGTH: 23
<212> TYPE: DNA
<213> ORGANISM: Newcastle disease virus

<400> SEQUENCE: 16
gtacatacag gccgatgtat tgc                                    23

<210> SEQ ID NO 17
<211> LENGTH: 23
<212> TYPE: DNA
<213> ORGANISM: Newcastle disease virus

<400> SEQUENCE: 17
aaggtctttt gttgcgcctt ttg                                    23

<210> SEQ ID NO 18
<211> LENGTH: 22
<212> TYPE: DNA
<213> ORGANISM: Newcastle disease virus

<400> SEQUENCE: 18
cgttagccaa gttgcgttag ag                                     22

<210> SEQ ID NO 19
<211> LENGTH: 19
<212> TYPE: DNA
<213> ORGANISM: Newcastle disease virus

<400> SEQUENCE: 19
ccgtcgaacc ctaacctcc                                         19

<210> SEQ ID NO 20
<211> LENGTH: 21
<212> TYPE: DNA
<213> ORGANISM: Newcastle disease virus

<400> SEQUENCE: 20
gtcttgcagt gtgagtgcaa c                                      21

<210> SEQ ID NO 21
<211> LENGTH: 21
<212> TYPE: DNA
<213> ORGANISM: Newcastle disease virus

<400> SEQUENCE: 21
cctcgcaagg tgtggtttct a                                      21

<210> SEQ ID NO 22
<211> LENGTH: 24
<212> TYPE: DNA
<213> ORGANISM: Newcastle disease virus

<400> SEQUENCE: 22
gccactcttc atagtcctta taca                                   24

<210> SEQ ID NO 23
```

```
<211> LENGTH: 25
<212> TYPE: DNA
<213> ORGANISM: Newcastle disease virus

<400> SEQUENCE: 23
ccatgagctg ttttgccttg tatct                                    25

<210> SEQ ID NO 24
<211> LENGTH: 22
<212> TYPE: DNA
<213> ORGANISM: Newcastle disease virus

<400> SEQUENCE: 24
gcacctatcc atgacccaga tt                                       22

<210> SEQ ID NO 25
<211> LENGTH: 23
<212> TYPE: DNA
<213> ORGANISM: Newcastle disease virus

<400> SEQUENCE: 25
cgatacaatg acacatgccc aga                                      23

<210> SEQ ID NO 26
<211> LENGTH: 24
<212> TYPE: DNA
<213> ORGANISM: Newcastle disease virus

<400> SEQUENCE: 26
gacctattgt ctcagcattg ctga                                     24

<210> SEQ ID NO 27
<211> LENGTH: 23
<212> TYPE: DNA
<213> ORGANISM: Newcastle disease virus

<400> SEQUENCE: 27
ggaaccaagt gtagatgtaa tct                                      23

<210> SEQ ID NO 28
<211> LENGTH: 23
<212> TYPE: DNA
<213> ORGANISM: Newcastle disease virus

<400> SEQUENCE: 28
gagggtattc gagtgcaacc tga                                      23

<210> SEQ ID NO 29
<211> LENGTH: 21
<212> TYPE: DNA
<213> ORGANISM: Newcastle disease virus

<400> SEQUENCE: 29
ggtcttcgcc taaggatgtt g                                        21

<210> SEQ ID NO 30
<211> LENGTH: 22
<212> TYPE: DNA
<213> ORGANISM: Newcastle disease virus

<400> SEQUENCE: 30
ctgaattctc cgaagagagt at                                       22
```

```
<210> SEQ ID NO 31
<211> LENGTH: 21
<212> TYPE: DNA
<213> ORGANISM: Newcastle disease virus

<400> SEQUENCE: 31
tgatcgcatg agcactggct g                                              21

<210> SEQ ID NO 32
<211> LENGTH: 19
<212> TYPE: DNA
<213> ORGANISM: Newcastle disease virus

<400> SEQUENCE: 32
ttgcagctgc aggaattgt                                                 19

<210> SEQ ID NO 33
<211> LENGTH: 22
<212> TYPE: DNA
<213> ORGANISM: Newcastle disease virus

<400> SEQUENCE: 33
ctatacagta tgaggtgtca ag                                             22

<210> SEQ ID NO 34
<211> LENGTH: 20
<212> TYPE: DNA
<213> ORGANISM: Newcastle disease virus

<400> SEQUENCE: 34
gaattgacta cagtattcgg                                                20

<210> SEQ ID NO 35
<211> LENGTH: 17
<212> TYPE: DNA
<213> ORGANISM: Newcastle disease virus

<400> SEQUENCE: 35
gcgcggtcca tgattga                                                   17
```

COMPOSITIONS AND METHODS FOR TREATMENT OF CANCER

CROSS-REFERENCE TO RELATED APPLICATIONS

This application is a continuation of International application PCT/IL02/00765 filed Sep. 12, 2002, the entire content of which is expressly incorporated herein by reference thereto.

FIELD OF THE INVENTION

The present invention relates to lentogenic strains of Newcastle Disease virus that have oncolytic activities, and the use of such viruses and/or isolated proteins derived from all strains of the NDV virus in the treatment of cancer.

BACKGROUND OF THE INVENTION

Viruses are known to exert an oncolytic effect on malignant cells and the use of oncolytic viruses as therapeutic agents has been reported (Csatary et al. *Cancer Detect Prev* (1993) 17(6):619–27; Csatary et al. *Anticancer Research* (1999) 19(1B):635–8 and for review see Sinkovics *J. of Clinical Virology* (2000) 16: 1–15).

Oncolytic viruses, for example the avian virus Newcastle Disease Virus (NDV), have been shown to be cytolytic to tumor cells in vivo and in vitro (Reichard et al. *J Surg Res* (1992) 52(5):448–53; Bar Eli et al. *J Cancer Res Clin Oncol* (1996) 122: 1–7 and Tsadok-David et al. (1995) *J. Cancer Research Clinical Oncology* 121:169–174).

The Newcastle disease virus is an avian RNA paramyxovirus that causes Newcastle disease in different avian species (dependent on the virulence of the virus strain and on the age of the individual bird), but that is considered minimally pathogenic in humans. NDV is an enveloped virus containing a linear, non-segmented, single-strand, negative sense RNA genome. The virion consists of a coiled nucleocapsid containing single stranded RNA and 6 structural polypeptides (M.W. 20,000–80,000). The nucleocapsids are coated with protein and lipid envelopes. The matrix protein (M), located in the inner surface of the viral envelope, is involved in viral assembly and interacts with both the viral membrane and the nucleocapsid proteins. On the outer surface of the viral envelope are two viral glycoproteins: the hemagglutinin-neuraminidase (HN) and the fusion glycoprotein (F). The HN glycoprotein is involved in the binding of the virus to cellular receptors. Monoclonal antibodies raised against this protein were shown to neutralize NDV infectivity. The F protein, which is first expressed as an inactive precursor (F0) and then cleaved post-translationally to produce two disulfide linked polypeptides (F1 and F2), is involved in penetration of NDV into host cells by facilitating fusion of the viral envelope with the host plasma cell membrane. Antisera to the F protein inhibited hemolysis and virus-induced cell fusion Since the F and HN glycoproteins play a crucial role in NDV infectivity, much effort has been done to clone NDV genes. EP Patent 227414 to Bingham et al., discloses the cDNA sequence encoding the F and HN polypeptides of NDV Beaudette C strain and envisages the use of this nucleotide sequence for the preparation of labelled probes, which will be utilized for diagnosis of NDV in poultry as well as for the preparation of the F and HN polypeptides.

The state of proteolytic cleavage of the surface glycoproteins F and HN is responsible for the virulence of the different NDV strains. F0 of virulent strains is cleaved to F1 and F2 in a wide range of host cells, whereas F0 of avirulent strains is cleaved only in few host cells. Accordingly, these differences are expressed in the classification of the different strains of NDV as velogenic (highly pathogenic), mesogenic (intermediate in pathogenicity) and lentogenic (apathogenic) strains.

In addition to their role in infectivity, the HN and F surface glycoproteins of NDV have also been postulated to be involved in the oncolytic capabilities of NDV (MSc thesis by Alissa Waldman-Kegnovitch (1999) Dept of Virology, Haddasa Medical School of the Hebrew University of Jerusalem).

The effect of oncolytic viruses on neoplastic cells is attributed by some to the enhancement of the sensitivity of the neoplastic cells to the cytolytic activity of tumor necrosis factors and to the immune stimulatory properties of these viruses. NDV in animals induces locally chemokines and cytolines such as tumor necrosis factor alpha that affect T cell recruitment and activation (Schirrmacher et al. (1998) *Semin Oncol* 25(6):677–96 and Schirrmacher et al. (1999) *Int J Oncol* 14(2):205–15). There are other reports that attribute the killing effect of an attenuated strain of NDV (73-T) on neuroblastoma cells to direct cytolysis following replication of infectious virus (Lorence et al. *J. Nat. Cancer Inst.* (1994) 86(16) 1228–1233). The killing effect of a mesogenic strain of NDV (RO) on Daudi lymphoma cells and the effect of NDV Ulster strain on metastatic Esb lymphoma and B16-F10 melanoma was found to be unrelated to viral replication since UV inactivated viruses were found to be as effective as infectious viruses in killing these tumor cells (Tsadok-David et al. (1995) *J. Cancer Research Clinical Oncology* 121:169–174 and Schirrmacher et al. (1997) *Clin Cancer Res* 3(7):1135–48).

Present efforts at cancer therapy using viruses involve the use of live pathogenic viruses as cytolytic agents (see Csatary et al. above and U.S. Pat. No. 5,602,023 to Csatary). WO 00/62735 of Pro-Virus discloses the use of any interferon sensitive strain of virus for killing neoplastic cells that are deficient in the interferon response. The Pro-Virus disclosure supplies a catalog of viral strains including three mesogenic strains of NDV (MK107, NJ Roakin, and Connecticut-70726) shown to be useful for treatment of human tumor xenografts in athymic mice. NDV administration to these mice caused tumor regression, which was attributed to more efficient and selective replication of NDV in tumor cells versus normal cells. The differential sensitivity of tumor cells to killing by NDV was disclosed to be correlated to an inability of the cells to manifest interferon-mediated antiviral response. The above patent application claims methods of infecting neoplasms or tumors and methods of treating neoplasms or tumors by interferonensitive, replication competent RNA or DNA viruses Alternative methods are mostly directed at developing vaccines for anti tumor immunization. For example, NDV is used in the preparation of an autologous tumor cell vaccine for humans (reviewed in Schirrmacher et al. (1998) *Semin Oncol* 25(6):677–96).

Nowhere in the background art is it taught or suggested that lentogenic strains of NDV are used for cancer therapy, or that surface glycoproteins derived from different strains of NDV, namely, velogenic, mesogenic or lentogenic strains, may have oncolytic properties and be useful in the treatment of cancer.

SUMMARY OF THE INVENTION

The compositions and methods of the invention utilize oncolytic properties of viruses and/or of viral proteins for the killing of neoplastic cells. The present invention provides compositions and methods for treatment of cancer that avoid contacting a patient with pathogenic strains of viruses.

The present invention provides a clonal lentogenic oncolytic strain of NDV, denoted herein HUJ, useful in treating cancer.

The present invention provides a pharmaceutical composition comprising at least one lentogenic oncolytic strain of NDV for treatment of cancer. The present invention further provides a pharmaceutical composition comprising at least one lentogenic oncolytic strain of NDV further comprising a suitable carrier.

Preferably, the HUJ strain of NDV (which is further described below) is utilized in the treatment of cancer. More preferably, the composition comprises $10^6-10^{12}$ egg infectious dose 50% $EID_{50}$) per each treatment dose of the HUJ NDV strain. Alternatively and preferably the treatment with the HUJ NDV will fall within the range of 20 $EID_{50}$/cell to 2000 $EID_{50}$/cell treated.

In an alternative embodiment the composition of the invention contains at least one isolated viral glycoprotein or a subunit or analog thereof having oncolytic activity. In a further embodiment, the viral glycoprotein is derived from NDV. According to another embodiment of the invention the composition comprises at least the F glycoprotein of NDV. The term F protein as used herein includes both F and F0. In a further embodiment the composition comprises the F glycoprotein and the hemagglutinin activity containing subunit of the HN glycoprotein of NDV. In yet a further embodiment the composition comprises the F glycoprotein and the HN glycoprotein of NDV. The term HN protein as used herein includes both HN and its precursor HN0, which is cleaved at its C-terminus to yield active HN. The viral glycoproteins utilized in this embodiment are non-infectious and can, therefore, be the product of any suitable stain of NDV. Preferably and alternatively, velogenic strains of NDV are used, alternatively and preferably, mesogenic strains, alternatively and preferably lentogenic strains. Further, the composition may comprise any combination of viral proteins or subunits or analogs thereof having oncolytic activity or a combination of whole lentogenic oncolytic NDV viruses and viral proteins or subunits or analogs thereof having oncolytic activity.

The present invention further provides methods for treatment of cancer utilizing the pharmaceutical compositions described above.

According to a further embodiment of the invention the treatment for cancer utilizes at least one isolated polynucleotide encoding at least one viral polypeptide or an analog or subunit thereof having oncolytic activity. In a further embodiment of the invention the treatment for cancer utilizes isolated polynucleotide encoding the F protein of NDV. In alternative embodiment, the isolated polynucleotide encoding for the HN protein of NDV is utilized. In a further embodiment a combination of the isolated polynucleotides encoding the F and HN glycoproteins are used.

It is known that the proteins F and HN are glycoproteins. The polynucleotides of the invention encode the polypeptide portion thereof, i.e., that portion which is subsequently glycosylated in vivo.

The F polypeptide is also processed in vivo by cleavage into the two shorter polypeptides F1 and F2. Accordingly, the invention encompasses a polynucleotide encoding F1 and F2 polypeptides as separate molecules or as a single disulfide bridged molecule or their bioprecursor F0 polypeptide.

It is explicitly to be understood that any fragment of the polypeptides that retains the oncolytic activity of the intact protein is within the scope of the present invention. Accordingly, the polynucleotides encoding any such fragment are within the scope of the invention According to the important aspect of the invention, there is provided an isolated polynucleotide encoding an F and/or HN polypeptide of NDV RNA, a bioprecursor of a said polypeptide or any active fragment of said polypeptide or an artificial polynucleotide complementary to the polynucleotide encoding an F and/or HN polypeptide of NDV RNA.

The invention further includes a host cell transfected or infected with recombinant polynucleotides as defined above.

The polynucleotides of the invention may be used as intermediates in the production of polypeptides by recombinant DNA technology. It is contemplated, therefore, that an expression vector of the invention containing an appropriate promoter and the polynucleotides of the invention, expressed for example in yeast or bacteria will give rise to the appropriate encoded polypeptides. Alternatively and preferably the vector may be a viral vector.

According to a further aspect of the invention a lentogenic strain of NDV, preferably the HUJ strain, is used in the preparation of a composition for the treatment of cancer. In another embodiment of the invention a viral glycoprotein or a subunit or analog thereof is used in the preparation of a composition for cancer treatment Preferably, the NDV coat glycoproteins, more preferably the F glycoprotein and/or the HN glycoprotein, are used.

The method of the invention for treatment of cancer, according to an embodiment of the invention, includes the step of administering to a patient a therapeutically effective amount of a composition comprising as an active ingredient a lentogenic oncolytic strain of NDV, preferably the HUJ strain, and/or at least one isolated viral protein as described above. The composition may be administered to the patient through any suitable route. One particularly preferred embodiment utilizes injection of the composition directly into a tumor or adjacent to the tumor.

Thus, the compositions and methods of the invention provide a treatment for cancer that does not share the risks that may be involved in the use of live velogenic (highly pathogenic) or even mesogenic (intermediate in pathogenicity) strains of viruses.

BRIEF DESCRIPTION OF THE DRAWINGS

The present invention will be understood and appreciated more fully from the following detailed description taken in conjunction with the drawings in which:

FIG. 10 shows the predicted amino acid sequence of the F and HN polypeptides.

DETAILED DESCRIPTION OF THE INVENTION

Figure 1:
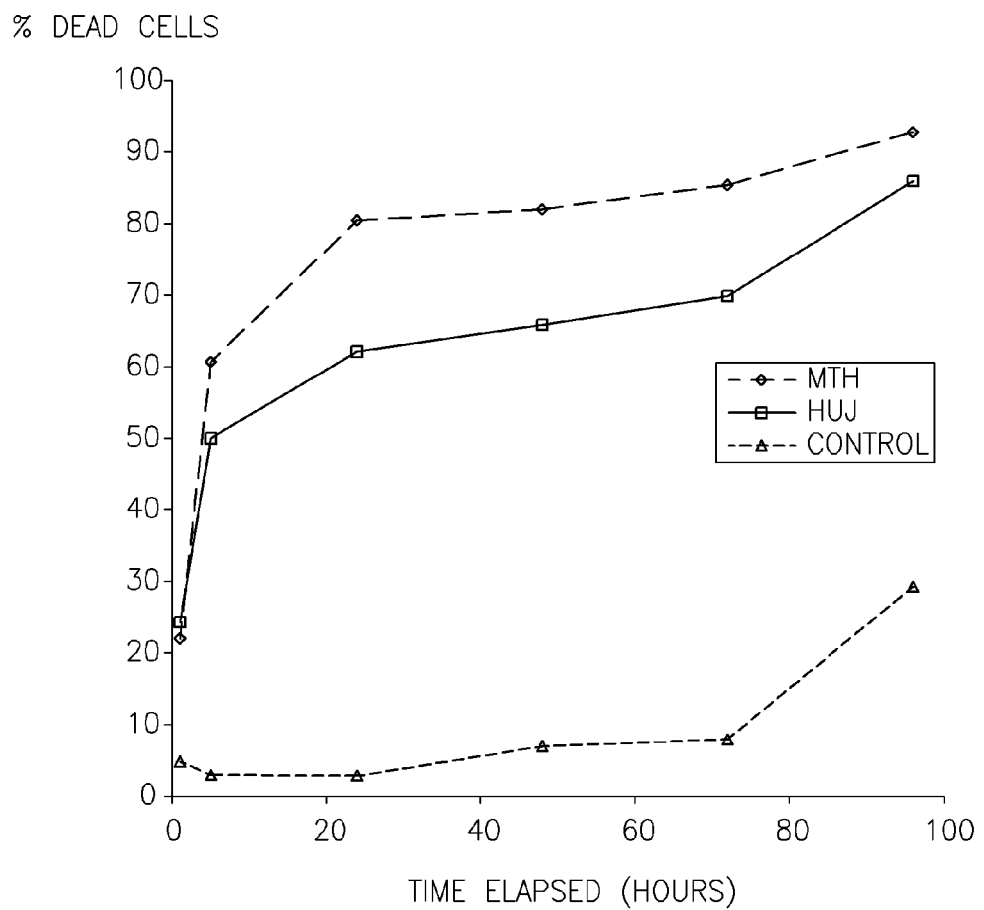
FIG. 1 is a graph showing the results of a representative experiment of the cytotoxic effect of two NDV strains (HUJ and MTH) on Daudi cells in culture.

Viruses are known to exert oncolytic effect on tumor cells and the use of oncolytic viruses as therapeutic agents has been reported. As described above, some effort has been done to use non-human viruses exhibiting medium to high pathogenicity for treatment of cancer. However, the use of apathogenic (lentogenic) non-human viruses or isolated viral proteins having oncolytic activity for treatment of cancer has not been reported in prior art. Thus, the present invention discloses compositions and methods for treatment of cancer that utilize the oncolytic properties of certain viruses and isolated viral components. The disclosed compositions and methods provide, for the first time, safe, effective and reliable means to treat cancer in an individual in need thereof. These methods overcome the drawbacks of using pathogenic strains of viruses for human therapy.

The present invention thus provides compositions and methods for treatment of cancer using lentogenic oncolytic strain of non-human virus, the Newcastle Disease virus (NDV). It further provides methods for treatment of cancer comprising isolated viral proteins or subunits or analogs thereof having oncolytic activity as well as isolated polynucleotides or constructs containing same, which encode for the viral proteins. The polynucleotides or constructs containing same may include any vector polynucleotide, including viral vector polynucleotide. The present invention provides host cells containing the polynucleotides, constructs containing same, and the vector polynucleotides as described above, which will also be used for treatment of cancer. The present invention further provides treatment of cancer using combination of any of the above.

A modified lentogenic NDV strain denoted herein as HUJ is disclosed below. It is desirable to obtain a clonal virus to ensure or increase its homogeneity. Clonal virus can be produced according to any method available to the skilled artisan, for example by limiting dilution or by plaque purification. According to an embodiment of the invention, a clonal HUJ strain prepared by limiting dilution is used in the preparation of a composition for the treatment of cancer, with or without an appropriate carrier such as human serum albumin (HSA) or any suitable adjuvant,. All types of cancers may be included in the scope of the present invention. As a non limiting example, the following cancers can be treated according to the present invention: glioblastoma, lung carcinoma, breast cancer, prostate, melanoma, leukemia and sarcomas.

The present invention provides compositions and methods for treatment of cancer utilizing at least one isolated viral proteins having oncolytic activity, preferably the F and HN glycoproteins of NDV. The F and HN glycoproteins were shown to play an important role in viral infectivity. However, nowhere in the prior art is it suggested that isolated F and HN proteins have oncolytic activities. The present invention provides, for the first time, direct evidence of the oncolytic effect of isolated viral proteins. According to the invention, viral proteins, preferably, the F and/or HN glycoproteins of NDV or analogs or subunits of these glycoproteins or mixtures thereof are used in the preparation of a composition for the treatment of cancer.

The term "oncolytic activity" as used herein includes cytotoxic effect in vitro and/or in vivo to tumor cells without any effect to normal cells. The cytotoxic effect under in vitro conditions is detected by various means as known in prior art, for example, by staining with a selective stain for dead cells, by inhibition of DNA synthesis or by apoptosis.

It should be appreciated by persons skilled in the art that the term "protein analog" includes peptides or polypeptides having the functionality of viral counterparts (i.e. fusion, hemagglutinin, and neuraminidase proteins, etc.) and not necessarily having the same sequence, secondary or tertiary structure as the viral counterparts. Thus, truncated or altered proteins displaying the oncolytic activity as the natural viral proteins, may be used in the composition and method of the present invention.

The fusion, hemagglutination and neuraminidase activities of the F and HN glycoproteins of NDV may be responsible for the oncolytic effect of the isolated proteins. However, the present invention encompasses other viral proteins exhibiting other activities that may be responsible for the oncolytic effect of isolated viruses.

The proteins can be used in a composition with an adjuvant such as alum hydroxide, emulsions or submicron emulsions (for example, U.S. Pat. Nos. 5,576,016, 5,662, 932, 5,716,637, 5,961,970) or other known pharmaceutical carriers such as human serum albumin. Also, genetically engineered viral proteins having oncolytic activity, preferably the viral fusion, hemagglutination and neuraminidase proteins are included in the scope of this invention.

The present invention provides compositions and methods for treatment of cancer comprising isolated polynucleotides and constructs containing same encoding the F and HN proteins of the HUJ strain of NDV. The nucleotide sequence encoding the F protein of HUJ was found to be almost identical (3 nucleotide difference) to the LaSota strain. Therefore, the present invention encompasses the use of isolated polynucleotide sequences encoding the F protein of other lentogenic strains.

The surface glycoproteins may be obtained from any naturally occurring strain of NDV. Preferably, the glycoproteins are obtained from a velogenic or a mesogenic NDV strain, such as the Roakin/46 VR 109 (RO) strain from the American type collection. Alternatively and preferably the glycoproteins from HUJ or other lentogenic strain are used. Also, the glycoproteins may be obtained from genetically or otherwise engineered virus strains. Furthermore, the glycoproteins may be obtained from an expression system exemplified by, but not limited to, a mammalian expression system, an insect expression system or a bacterial expression system. Alternatively, synthetic proteins or recombinant viral proteins, such as HN or F, may be used in the present invention.

The composition may be in any form suitable for administration to a patient, such as a suspension, an emulsion, a spray, a solution or any other formulation according to principles well known in the art. The compositions of the invention may be adapted for any suitable route of administration, including but not limited to intravenous, oral, buccal, intranasal, inhalation, topical application to a mucosal membrane or injection, including intradermal, intrathecal, intracisternal, intralesional or any other type of injection.

The method of the invention for treatment of cancer, according to an embodiment of the invention, includes the step of administering to a patient a therapeutically effective amount of HUJ NDV. The HUJ NDV may be administered to the patient through any suitable route, as described above. One particularly preferred embodiment utilizes injection of the HUJ strain or a composition comprising the HUJ strain and/or at least one viral glycoprotein as described above directly into a tumor or adjacent to the tumor.

According to another embodiment of the invention the method of the invention for treatment of cancer, includes the step of administering to a patient (through any suitable route, as described above) a therapeutically effective amount of at least one viral glycoprotein of NDV or a subunit or analog thereof having oncolytic activity. The viral glycoprotein may include at least the F glycoprotein of NDV, the HN glycoprotein of NDV or the F glycoprotein and the HN glycoprotein of NDV.

Treatment of patients with cancer, in accordance with embodiments of the present invention, can be systemic, where the above compositions or even isolated whole viruses and/or isolated proteins are administered to the patient The form of administration may be intravenous, oral, buccal, intranasal, inhalation, topical application to a mucosal membrane, or injection, including intradermal, intrathecal, intracisternal, intralesional or any other type of injection. Preferably, lentogenic NDV viruses (such as the HUJ strain), or viral proteins as described above or compositions according to the invention, are administered locally and directly to a tumor or to its vicinity. Typically, the form of local administration is by injection, for example, intralesional injection.

The isolated polynucleotides of the present invention are used in the production of at least one viral polypeptide or an analog or subunit thereof having oncolytic activity by recombinant DNA technology in cells transfected with these polynucleotides. Preferably, the polynucleotides used in the production of the F and/or HN polypeptides of NDV HUJ. The polynucleotides may also consist of an expression vector, for example a viral vector, to achieve the polypeptide expression. The methods for expression of viral NDV proteins are disclosed in EP 227414 to Bingham and are fully incorporated herein.

The term "polynucleotide" includes single-stranded and double-stranded DNA, RNA and chemically or biosynthesized nucleotide polymers of varying lengths from 16 nucleotides upwards.

The term "artificial" as used herein signifies the intervention of man, by any means, in the production of the polynucleotide. In addition to artificial polynucleotides per se, the invention includes recombinant molecules. These can be broadly defined as consisting of vector polynucleotides and polynucleotide foreign thereto, the foreign polynucleotide consisting of or including a polynucleotide of the invention as defined above. Normally, the polynucleotide is DNA and the invention includes particularly DNA wherein the vector is a cloning vector or an expression vector. The expression vector can be, for example, a prokaryotic cell expression vector or eukaryotic cell expression vector. The term "vector" herein also includes shuttle vectors. Where expression is required, the polynucleotide will additionally contain a signal sequence of the kind effective for translation and other processing of the mRNA into the desired viral proteins.

The present invention provides the isolated polynucleotides encoding viral proteins having oncolytic activity, preferably, the F and HN glycoproteins, which are introduced into host cells as to be expressed by the cells and/or their progeny, and the recombinant cells are then administered in vivo for therapeutic effect To introduce these genes into cells, it is desired to improve membrane permeability for the oligonucleotides. To improve membrane permeability various means are known in the art For instance, the oligonucleotide molecule may be linked to a group, which includes partially unsaturated aliphatic hydrocarbon chain and one or more polar or charged groups such as carboxylic acid groups, ester groups, and alcohol groups. Alternatively, oligonucleotides may be linked to peptide structures, which are preferably membranotropic peptides. Such modified oligonucleotides penetrate membranes more easily, which is critical for their function and may, therefore, significantly enhance their activity.

To enhance uptake of oligonucleotides across cell membranes additives may be selected. Such agents are generally agents that will enhance cellular uptake of double-stranded DNA molecules. For instance, certain lipid molecules have been developed for this purpose, including the transfection reagents DOTAP (Boehringer Mannheim), Lipofectin, Lipofectam, and Transfectam, which are available commercially.

Another way of enhancing membrane permeability is by conjugating oligonucleotides to molecules that are known to bind to cell surface receptors. Examples of suitable groups for forming conjugates are sugars, vitamins, hormones, cytokines transferrin, asialoglycoprotein, and the like molecules. For example, Low et al U.S. Pat. No. 5,108,921 describes the use of these molecules for the purpose of enhancing membrane permeability of peptides, proteins and oligonucleotides, and the preparation of said conjugates.

Having now generally described the invention, the same will be more readily understood through reference to the following examples, which are provided by way of illustration and are not intended to be limiting of the present invention.

EXAMPLES

HUJ Strain of NDV

A sample of NDV HUJ (Master Virus Bank) has been deposited under the Budapest Treaty on Jul. 24, 2006 at the European Collection of Cell Cultures (ECACC), Vaccine Research and Production Laboratory, Public Health Laboratory Services, Centre for Applied Microbiology and Research, Porton Down, salisbury, Wiltshire SP40JG, United Kingdom, and was assigned reference number, 06072401. A sample of the virus was passaged in hen's eggs and was shown to be viable.

The virus was derived from naturally lentogenic B1 strain of NDV obtained as ATCC V188. The virus was passaged four times in hen's eggs to prepare a research stock. The infected allantoic fluid from the fourth passage (E4 stock) was stored at −70° C. The infected allantoic fluid from the E4 stock underwent 50 regular passages in 10–11 day old embryonated eggs. The allantoic fluid was labeled "NDV lento" and was divided into vials stored at −80° C. The "NDV lento" was cloned in 10–11 days old embryonated eggs by limiting dilution. Allantoic fluid from the egg infected with the highest dilution was labeled "NDV lento (cloned)" and was stored at −70° C. Studies of the cytotoxicity of the "NDV lento (cloned)" strain were carried out in Daudi cells and normal human cells. The strain was shown to be oncolytic and was renamed "NDV HUJ". The intracerebral pathogenicity index (ICPI) of the "NDV HUJ" strain was tested in 1 day old chicks and was shown to be 0.0, indicating that the virus can be classified as lentogenic, non-virulent, non-pathogenic.

The HUJ strain was compared to MTH-68/H strain of NDV, which is an attenuated strain obtained by serial passages through eggs (allantoic fluid), manufactured in Hungary by Phylaxia-Sanofi (Csatary et al. *Anticancer Research* (1999) 19(1B):635-S). Allantoic fluid containing virus and virus purified on sucrose gradients, were compared.

Preparation of the HUJ strain for in vitro studies: Serial passages were carried out at limiting dilutions in 10–11 day old chicken embryonated eggs. Allantoic fluid from the highest dilution (in which only 1/6 eggs is virus positive) was collected and further passaged in serial dilutions. Cultivation, concentration and purification were carried out using routine methods (Tzadok-David et al. and Slosaris M., Levy B., Katz E., Levy R, Zakay-Rones Z. (1989) *Avian Dis.* 33:248–253).

From 750 incubated eggs about 640 embryonated eggs (10–11 days) were inoculated into the allantoic cavity with $10^5$–$10^6$ embryo infectious dose 50% ($EID_{50}$)/egg. Embryos dying within the first 24 hr were discarded. After 72 hr, eggs with live embryos only were chilled at 4° for 16–18 hr. The allantoic fluid (~3 liters) was collected and centrifged for 20 min at 2,000 rpm to remove debris and the supernatant with hemagglutination titer (HA) of 640–1280/ml was saved.

The virus was concentrated by centrifigation from infected allantoic fluid at 18,000 rpm in a Sorvall (RC-5) centrifuge using a SS-34 rotor, for 60 min at 4° C. The concentrated virus (100 ml—containing 32,000 HA units) was then purified by centrifugation for 90 min at 24000 rpm through a sucrose gradient (10–60%) with an ultra centrifige in a SW-27 rotor. The bands containing virus were collected, pelleted in an SW-27 rotor for 60 min at 24,000 rpm, resuspended, and the purified virus suspension was passed through Millipore filters, aliquoted in 0.5 ml and kept at −70° C. until use.

It will be appreciated by persons skilled in the art that other methods of virus concentration and purification may be used for obtaining the results above.

Preparation of virus for clinical studies: The HUJ strain also referred to as "NDV lento (clone)" was further cloned twice by limiting dilution in 10–11 day old embryonated SPF (specific pathogens free) eggs (obtained from ALPES (Aves Libres de Patógenos Especificos S.A. de C.V), Pueblo, Mexico, a subsidiary of SPAFAS Charles River Lab.) to produce a Virus Master Seed Bank consisting of 220 tubes. The tubes are stored at −80° C. and contain the harvested allantoic fluid frozen without any further purification. One tube from the Master seed bank is expanded into a Virus Working Seed Bank consisting of 300 tubes following the same procedure as used in the production of the master bank. The working bank tubes are stored at −80° C. The tubes contain the harvested allantoic fluid frozen without any further purification.

The starting material for the virus production is a vial of the NDV HUJ Working Bank and 10–11 day old embryonated SPF eggs.

One production run using approximately 3000 eggs would produces the amount of material needed for the clinical study. The production was divided into several harvests (~500 eggs). For each harvest, a vial of working bank was thawed and the virus suspension was diluted in Gibco PBS ($10^5 EID_{50}$/egg). A small hole was manually punched in the top of the egg and an aliquot of the virus suspension was injected into the amino-allantoic cavity of the egg. The hole in each egg was sealed with sterile acrylic cement and the eggs were incubated for 72 hrs. The eggs were checked for viability. Eggs which appeared upon candling to have died within the last 12–24 hrs were set aside for harvesting and eggs which had appeared to have died earlier were discarded. If the percent of all eggs that had died since the time of inoculation exceeded 25%, then all viable eggs were harvested along with the newly dead eggs. If the percent egg death was less than 25%, viable eggs were incubated for a further 24 hours and after which the newly dead and viable eggs were harvested. Harvesting consisted of removing the top of the egg, inspecting the embryo and allantoic fluid and pippeting the allantoic fluid into 50 ml bottles. If the allantoic fluid taken up into the pipette was not clear it was rejected. The harvested allantoic fluid was clarified by low speed centrifugation and stored at 4–7° C. Aliquots of the collected infected allantoic were tested for sterility and titer ($EID_{50}$ and hemagglutination).

The total amount of virus obtained from a particular harvest was determined by the number of eggs harvested, the volume of the allantoic fluid harvested and the titer. Starting with about 450 eggs, 150–300 eggs were harvested. The yield of harvested fluids was about 8–10 ml per egg and the volumes of collected fluids from individual harvests varied from 1000 to 3280 ml. Titers ranged from $10^{9.3}$/ml to $10^{10.2}$/ml $EID_{50}$ and the total amount of virus in crude bulk harvests ranged from $6.4 \times 10^{12}$ to $1.6 \times 10^{13}$ $EID_{50}$. The total amount of virus in the five crude bulk harvests was $5.8 \times 10^{13}$ $EID_{50}$ at the time of harvesting. The virus was then concentrated by high speed centrifugation and purified in sucrose gradients as follows:

Clarified crude bulk virus after having been stored at 4–7° C. for between 1–6 weeks was re-clarified by low speed centrifugation (3000 rpm 30 min). Aliquots of re-clarified bulk from each harvest were taken and stored at −80° C. for further testing and additional aliquots were taken for in-process sterility testing. The re-clarified bulk was then centrifuged at high speed 12,500 rpm for 1.5 hrs at 4° C. and the pelleted virus was re-suspended in Gibco Dulbeco PBS. Titers were determined to obtain total recovery. A total of 12,260 ml of reclarified bulk fluids from five harvests were concentrated to a total of 100 ml of resuspended pelleted virus with a 50% average yield based on $EID_{50}$ titers, ranging from 29% to 82% yields for individual harvests. Sterility was tested on aliquots from each tube of re-suspended concentrated virus. All samples of the concentrated virus passed sterility testing.

For purification, the concentrated virus was centrifged at ultra-high speed in a 20/40/60% sucrose gradient at 22,000 rpm for 2.5 hrs at 4° C. In a typical ultracentrifuge tube, approximately 8 ml of concentrated virus is layered on top of 24 ml of sucrose gradient. The purified virus is recovered as a band of approximately 4.7 ml. The band of concentrated virus is suspended in approximately 10 ml of sterile saline, whose pH had been adjusted to 7.6–7.8 by addition of autoclaved solution of disodium phosphate prepared in water for infusion. Sucrose solutions were prepared by dissolving endotoxin-free sucrose in Gibco Dulbeco PBS and autoclaving. Clinical dosages were prepared from combined harvests of purified virus by diluting the viral suspension with sterile saline to achieve a concentration of approximately $1 \times 10^{10}$ EID$_{50}$/ml.

PCR and Sequencing of the F and HN genes: The nucleotide sequences determined for the F and HN genes of NDV HUJ-master bank and purified virus can be compared to related nucleotide sequence of the LaSota strain of Newcastle disease virus, which consists of 15186 base pairs of linear RNA. Viral RNA was extracted from the Newcastle disease virus HUJ master seed using the QIAGEN QIAamp viral RNA kit according to the manufacturer's instructions. A single stranded DNA copy of the viral RNA template was prepared using a standard protocol for production of cDNA from RNA template using reverse transcriptase. Briefly, two reaction mixtures were prepared. One mixture comprised 6.5 µl of dH$_2$O and 1 µl of the primer MSF1 (see below). The other mixture comprised 4.0 µl of 5× RT buffer (reverse transcriptase buffer), 4.0 µl dH$_2$O, 1.0 µl 40 mM NTPs (nucleotide triphosphates), 0.5 µl MMLV-RT (enzyme) and 0.5 µl RNAsin (RNAse inhibitor). A volume of 2.5 µl of RNA was added to the 7.5 µl of mix one, centrifuged briefly, heated at 95° C. for two minutes and placed on ice. A volume of 10 µl of mix two was added to the RNA/primer solution and incubated at 37° C. for 1 hour. The cDNA produced was used to prepare three overlapping PCR DNA fragments for each gene. The sequences of these primers in the viral genome are given below. Each PCR reaction mixture comprised 25µl PCR Ready mix x2 (AB gene Corp.), 18 µl DH$_2$O, and 1 µl of 1 µl of forward primer and 1 µl of reverse primer. The components were mixed, spun briefly and 5 µl appropriate cDNA added before thermal cycling. Cycling parameters were 94° C. for 10 minutes (one cycle), 94° C. (1 minute), 50° C. (1 minute) and 72° C. (3 minutes) for 29 cycles and 72° C. for 5 minutes. After the PCR, reaction mixtures were electrophoresed on an agarose gel and visualized using a UV transilluminator. DNA fragments size was estimated by comparing with marker DNA and fragments were purified. DNA fragments were excised from the gel and purified using the Qiaquick gel extraction kit (Qiagen cat no. 28706).

For DNA sequencing, a reaction mix was prepared comprising terminator ready reaction mix (4 µl; Applied Biosystems Corp), the PCR product (2–4 µl depending on its concentration), sequencing primer (1.6 µl) and deionised water to bring the total volume to 10 µl. The mixture was then incubated in a PCR machine using the program 'BIGD'. The sequenced products were precipitated by adding 1 µl of 25 mM glycogen and 52 µl of 2M sodium acetate pH 4.5. The mix was vortexed, left for 10 minutes and then centrifuged at 13,000 rpm for 30 minutes. The liquid was aspirated off leaving behind a pellet, which was rinsed by the addition of 150 µl of 80% ethanol. Following centrifugation at 13,000 for 10 minutes, the alcohol was removed and the sample centrifuged again before removing any remaining alcohol with a 10 pipette. The pellet was dried by heating on a block at 95° C. for 2 minutes, resuspended in 15 µl TSR, vortexed and then centrifuged (pulse) before heating again at 95° C. for 2 minutes and chilling on ice. Following an additional vortex and spin, samples were transferred to ABI tubes and then into the genetic analyzer (ABI PRISM™ 310 genetic analyzer). Data from the automated sequencer was edited using DNASTAR/SeqMan to obtain a consensus sequence. Sequences were aligned with the published sequence of a similar virus, for example B1 or LaSota,.

The PCR and sequencing primers were the following:

PCR primers for the F gene:

| Reference | Sequence | Position |
|---|---|---|
| MSF1 | TGACCACGAGGTTACCTCTAC | (1057 matrix protein, forward) SEQ ID NO. 3 |
| 2FOV | TCCAAGTAGGTGGCACGCATA | (957, reverse) SEQ ID NO. 4 |
| 3FOV | AATTGACTACAGTATTCGGACC | (693, forward) SEQ ID NO. 5 |
| 4FOV | TGTTGACATTCCCAAGCTCAG | (1460, reverse) SEQ ID NO. 6 |
| 5FOV | GCTCAGTCATCGCTAACTGC | (1209, forward) SEQ ID NO. 7 |
| 6FOV | CGG AAT ATC AAG CGC CAT GTA | (168 of HN gene, reverse) SEQ ID NO. 8 |

Sequencing primers for F gene:

| | | |
|---|---|---|
| 1FOV | TTAGAAAAAACACGGGTAGAA | (0, forward) SEQ ID NO. 9 |
| 7FOV | ACAGGACATTGACCACTTTGC | (300, forward) SEQ ID NO. 10 |
| 8FOV | CAGGTAACTCTACCTTCAGTCG | (902, forward) SEQ ID NO. 11 |
| 9FOV | CAACTCGATCAGTAATGCTTTGA | (1459, forward) SEQ ID NO. 12 |
| 10FOV | CCTAGATCAGATGAGAGCCAC-TACA | (1675, forward) SEQ ID NO. 13 |
| 11FOV | CTGCTGCATCTTCCCAACTG | (598, reverse) SEQ ID NO. 14 |
| 12FOV | GACTCTTGTATCCTACGGATAGA | (360, reverse) SEQ ID NO. 15 |
| 13FOV | GTACATACAGGCCGATGTATTGC | (1162, reverse) SEQ ID NO. 16 |
| 14FOV | AAGGTCTTTTGTTGCGCCTTTTG | (1653, reverse) SEQ ID NO. 17 |

PCR primers for the HN gene:

| | | |
|---|---|---|
| 1HNOV | CGTTAGCCAAGTTGCGTTAGAG | (103, forward) SEQ ID NO. 18 |
| 2HNOV | CCGTCGAACCCTAACCTCC | (927, reverse) SEQ ID NO. 19 |
| 3HNOV | GTCTTGCAGTGTGAGTGCAAC | (799, forward) SEQ ID NO. 20 |
| 4HNOV | CCTCGCAAGGTGTGGTTTCTA | (1548, reverse) SEQ ID NO. 21 |
| 5HNOV | GCCACTCTTCATAGTCCT-TATACA | (1397, forward) SEQ ID NO. 22 |
| 6HNOV (6HNOV) | CCATGAGCTGTTTTGCCTTG-TATCT | (intergenic HN/L, reverse) SEQ ID NO. 23 |

Sequencing primers for HN gene

| | | |
|---|---|---|
| 7HNOV | GCACCTATCCATGACCCAGATT | (464, forward) SEQ ID NO. 24 |
| 8HNOV | CGATACAATGACACATGCCCAGA | (1106, forward) SEQ ID NO. 25 |
| 9HNOV | GACCTATTGTCTCAGCATTGCTGA | (1708, forward) SEQ ID NO. 26 |
| 10HNOV | GGAACCAAGTGTAGATGTAATCT | (319, reverse) SEQ ID NO. 27 |
| 11HNOV | GAGGGTATTCGAGTGCAACCTGA | (621, reverse) SEQ ID NO. 28 |
| 12HNOV | GGTCTTCGCCTAAGGATGTTG | (1247, reverse) SEQ ID NO. 29 |
| 13HNOV | CTGAATTCTCCGAAGAGAGTAT | (1761, reverse) SEQ ID NO. 30 |
| 14HNOV | TGATCGCATGAGCACTGGCTG | (1964, reverse) SEQ ID NO. 31 |

Biological assay: The hemagglutination and infectivity titers of the HUJ virus were determined by the routinely used methods (Sever J L. 1962 J. Immunol. 80:320–329 for hemagglutination). Infectivity was determined by inoculation of serial dilutions into the allantoic sac of embryonated eggs and checking the fluids for hemagglutination 72 hrs post inoculation. The virus titer, defined as 50% endpoint egg infectious dose ($EID_{50}$) was calculated by the method of Reed and Muench (Reed L J Muench H A 1938, Amer. J Hyg 27:493–497). Stocks were prepared and stored at −70° C.

Sterility tests: The HUJ viral suspension was tested for bacterial and mycoplasma presence and was found to be sterile.

Nucleotide and amino acid sequences of the F and HN genes of HUJ: The 3358 nucleotide sequence, corresponding to 4498 to 7855 of the LaSota complete genome and covering all of the F gene, the intergene and most of the HN gene of HUJ is given below (SEQ ID NO:1):

```
   1  ACGGGTAGAA GATTCTGGAT CCCGGTTGGC GCCCTCCAGG TGCAAGATGG
  51  GCTCCAGACC TTCTACCAAG AACCCAGCAC CTATGATGCT GACTATCCGG
 101  GTTGCGCTGG CACTGAGTTG CATCTGTCCG GCAAACTCCA TTGATGGCAG
 151  GCCTCTTGCA GCTGCAGGAA TTGTGGTTAC AGGAGACAAA GCCGTCAACA
 201  TATACACCTC ATCCCAGACA GGATCAATCA TAGTTAAGCT CCTCCCGAAT
 251  CTGCCCAAGG ATAAGGAGGC ATGTGCGAAA GCCCCCTTGG ATGCATACAA
 301  CAGGACATTG ACCACTTTGC TCACCCCCCT TGGTGACTCT ATCCGTAGGA
 351  TACAAGAGTC TGTGACTACA TCTGGAGGGG GGAGACAGGG GCGCCTTATA
 401  GGCGCCATTA TTGGCGGTGT GGCTCTTGGG GTTGCAACTG CCGCACAAAT
 451  AACAGCGGCC GCAGCTCTGA TACAAGCCAA ACAAAATGCT GCCAACATCC
 501  TCCGACTTAA AGAGAGCATT GCCGCAACCA ATGAGGCTGT GCATGAGGTC
 551  ACTGACGGAT TATCGCAACT AGCAGTGGCA GTTGGGAAGA TGCAGCAGTT
 601  TGTTAATGAC CAATTTAATA AAACAGCTCA GGAATTAGAC TGCATCAAAA
 651  TTGCACAGCA AGTTGGTGTA GAGCTCAACC TGTACCTAAC CGAATTGACT
 701  ACAGTATTCG GACCACAAAT CACTTCACCT GCTTTAAACA AGCTGACTAT
 751  TCAGGCACTT TACAATCTAG CTGGTGGAAA TATGGATTAC TTATTGACTA
 801  AGTTAGGTGT AGGGAACAAT CAACTCAGCT CATTAATCGG TAGCGGCTTA
 851  ATCACCGGTA ACCCTATTCT ATACGACTCA CAGACTCAAC TCTTGGGTAT
 901  ACAGGTAACT CTACCTTCAG TCGGGAACCT AAATAATATG CGTGCCACCT
 951  ACTTGGAAAC CTTATCCGTA AGCACAACCA GGGGATTTGC CTCGGCACTT
1001  GTCCCAAAAG TGGTGACACA GGTCGGTTCT GTGATAGAAG AACTTGACAC
1051  CTCATACTGT ATAGAAACTG ACTTAGATTT ATATTGTACA AGAATAGTAA
1101  CGTTCCCTAT GTCCCCTGGT ATTTATTCCT GCTTGAGCGG CAATACGTCG
1151  GCCTGTATGT ACTCAAAGAC CGAAGGCGCA CTTACTACAC CATACATGAC
1201  TATCAAAGGT TCAGTCATCG CCAACTGCAA GATGACAACA TGTAGATGTG
1251  TAAACCCCCC GGGTATCATA TCGCAAAACT ATGGAGAAGC CGTGTCTCTA
```

```
                         -continued
1301     ATAGATAAAC AATCATGCAA TGTTTTATCC TTAGGCGGGA TAACTTTAAG

1351     GCTCAGTGGG GAATTCGATG TAACTTATCA GAAGAATATC TCAATACAAG

1401     ATTCTCAAGT AATAATAACA GGCAATCTTG ATATCTCAAC TGAGCTTGGG

1451     AATGTCAACA ACTCGATCAG TAATGCTTTG AATAAGTTAG AGGAAAGCAA

1501     CAGAAAACTA GACAAAGTCA ATGTCAAACT GACTAGCACA TCTGCTCTCA

1551     TTACCTATAT CGTTTTGACT ATCATATCTC TTGTTTTTGG TATACTTAGC

1601     CTGATTCTAG CATGCTACCT AATGTACAAG CAAAAGGCGC AACAAAAAAC

1651     CTTATTATGG CTTGGGAATA ATACTCTAGA TCAGATGAGA GCCACTACAA

1701     AAATGTGAAC ACAGATGAGG AACGAAGGTT TCCCTAATAG TAATTTGTGT

1751     GAAAGTTCTG GTAGTCTGTC AGTTCAGAGA GTTAAGAAAA AACTACCGGT

1801     TGTAGATGAC CAAAGGACGA TATACGGGTA GAACGGTAAG AGAGGCCGCC

1851     CCTCAATTGC GAGCCAGGCT TCACAACCTC CGTTCTACCG CTTCACCGAC

1901     AACAGTCCTC AATCATGGAC CGCGCCGTTA GCCAAGTTGC GTTAGAGAAT

1951     GATGAAAGAG AGGCAAAAAA TACATGGCGC TTGATATTCC GGATTGCAAT

2001     CTTATTCTTA ACAGTAGTGA CCTTGGCTAT ATCTGTAGCC TCCCTTTTAT

2051     ATAGCATGGG GGCTAGCACA CCTAGCGATC TTGTAGGCAT ACCGACTAGG

2101     ATTTCCAGGG CAGAAGAAAA GATTACATCT ACACTTGGTT CCAATCAAGA

2151     TGTAGTAGAT AGGATATATA AGCAAGTGGC CCTTGAGTCT CCGTTGGCAT

2201     TGTTAAATAC TGAGACCACA ATTATGAACG CAATAACATC TCTCTCTTAT

2251     CAGATTAATG GAGCTGCAAA CAACAGTGGG TGGGGGCAC CTATCCATGA

2301     CCCAGATTAT ATAGGGGGA TAGGCAAAGA ACTCATTGTA GATGATGCTA

2351     GTGATGTCAC ATCATTCTAT CCCTCTGCAT TTCAAGAACA TCTGAATTTT

2401     ATCCCGGCGC CTACTACAGG ATCAGGTTGC ACTCGAATAC CCTCATTTGA

2451     CATGAGTGCT ACCCATTACT GCTACACCCA TAATGTAATA TTGTCTGGAT

2501     GCAGAGATCA CTCACATTCA TATCAGTATT TAGCACTTGG TGTGCTCCGG

2551     ACATCTGCAA CAGGGAGGGT ATTCTTTTCT ACTCTGCGTT CCATCAACCT

2601     GGACGACACC CAAAATCGGA AGTCTTGCAG TGTGAGTGCA ACTCCCCTGG

2651     GTTGTGATAT GCTGTGCTCG AAAGTCACGG AGACAGAGGA AGAAGATTAT

2701     AACTCAGCTG TCCCTACGCG GATGGTACAT GGGAGGTTAG GGTTCGACGG

2751     CCAGTACCAC GAAAAGGACC TAGATGTCAC AACATTATTC GGGGACTGGG

2801     TGGCCAACTA CCCAGGAGTA GGGGGTGGAT CTTTTATTGA CAGCCGCGTA

2851     TGGTTCTCAG TCTACGGAGG GTTAAAACCC AATTCACCCA GTGACACTGT

2901     ACAGGAAGGG AAATATGTGA TATACAAGCG ATACAATGAC ACATGCCCAG

2951     ATGAGCAAGA CTACCAGATT CGAATGGCCA AGTCTTCGTA TAAGCCTGGA

3001     CGGTTTGGTG GGAAACGCAT ACAGCAGGCT ATCTTATCTA TCAAGGTGTC

3051     AACATCCTTA GGCGAAGACC CGGTACTGAC TGTACCGCCC AACACAGTCA

3101     CACTCATGGG GGCCGAAGGC AGAATTCTCA CAGTAGGGAC ATCTCATTTC

3151     TTGTATCAAC GAGGGTCATC ATACTTCTCT CCCGCGTTAT TATATCCTAT

3201     GACAGTCAGC AACAAAACAG CCACTCTTCA TAGTCCTTAT ACATTCAATG
```

-continued

3251 CCTTCACTCG GCCAGGTAGT ATCCCTTGCC AGGCTTCAGC AAGATGCCCC

3301 AACTCGTGTG TTACTGGAGT CTATACAGAT CCATATCCCC TAATCTTCTA

3351 TAGAAACC

The amino acid sequence derived from the above nucleotide sequence is given in FIG. 10 (SEQ ED NO:2). It will be noted that asterisks in this sequence mark stop codons. Thus the F protein will terminate at residue number 553.

The amino acid sequence has the fusion protein cleavage site motif from amino acid #109 to #119 of SGGGRQGR-LIG inferred from the nucleotides sequence starting at nucleotide 370, which is characteristic of lentogenicity.

The 3358 nucleotides of the virus from the Master Virus Bank matched those of the La Sota strain of NDV (gi: 3386504), except for nucleotide positions 111, 1006 and 1648 in the F gene.

Sequence of the F Gene of the Virus after Virus Purification on a Sucrose Gradient:

The nucleotide sequence of virus from production batch, obtained after purification of the virus on a sucrose gradient, as described above, was determined as follows: Viral RNA was extracted from the Newcastle disease virus HUJ using the SV Total Isolation kit (Promega) according to the manufacturer's instructions. The RNA was subjected to RT-PCR amplification with 4 different oligonucleotide primers. (Using Access Quick RT-PCR System, Promega). The sequences of these primers and their location in the viral genome are given below.

Each reaction mixture comprised of 25 μl RT-PCR Ready mix x2, 8μl RNA, 5 μl of each forward and reverse sequencing primer and 7 μl DDH20. The components were well mixed and spun briefly prior to subjection to the RT-PCR reaction (48° C. for 45 minutes for the RT reaction). Cycling parameters for the PCR were 94° C. for 2 minutes (one cycle), 94° C. (30 seconds), 60° C. (1 minute) and 68° C. (2 minutes) for 40 cycles and 68° C. for 7 minutes. The PCR reaction mixes were loaded on 1% agarose gel and visualized using a UV Tran illuminator. Band size was estimated by comparing with DNA marker. DNA fragments were excised from the gel and purified using the Mini-elute Gel extraction kit (Qiagen). Each fragment was resuspended in ddH20. The DNAs were subjected to Sequencing analysis. The RT-PCR and sequencing primers were virus had not changed in this region during the production process. It also provides confirmatory evidence for the relevant sequence.

Biological Characterization (MTH Compared with HUJ)

1) Hemagglutination and Neuraminidase Activities

TABLE 1

|  | Allantoic fluid | | Purified NDV | |
| --- | --- | --- | --- | --- |
| NDV strain | HA* | NA* | HA* | NA* |
| MTH | 1024 | 100 | 16,000 | 1,400 |
|  | 1024 | 384 |  |  |
| HUJ | 1024 | 300 | 32–64,000 | <2,400 |
|  | 1024 | <1000 |  |  |

*reciprocal titer of the dilution of hemagglutination (HA) and Neuraminidase (NA) activities. Neuraminidase is determined according to Aymard-Henry M et al 1973 Bull Wld Org 48: 199–202 and Warren LJ J Biol Chem 1959 234: 1971–1975. This assay measures the free sialic acid liberated by the viral enzyme neuraminidase from a substrate (fetuine).

TABLE 2

Comparison of neuraminidase activities of two NDV strains

| Virus dilution | MTH | HUJ |
| --- | --- | --- |
| 1:50 | 0.55* | 1.2 |
| 1:100 | 0.37 | 0.55 |
| 1:200 | 0.15 | 0.41 |

*OD at A 450 nm is correlated with neuraminidase enzyme activity.

These results (Tables 1 and 2) indicate that neuraminidase activity is higher in the HUJ strain compared to the MTH strain.

```
NDV-1  TT G C A G C T G C A G G A A T T GT        (4653 forward)
                                                   SEQ ID NO. 32

NDV-2  C T A T A C A G T A T G A G G T G T C A A G  (5540 reverse)
                                                   SEQ ID NO. 33

NDV-4  G A A T T G A C T A C A G T A T T C G G      (5189 FORWARD)
                                                   SEQ ID NO. 34

NDV-5  G C G C G G T C C A T G A T T G A           (6406 reverse)
                                                   SEQ ID NO. 35
```

The 1504 nucleotide sequence of the purified virus, corresponding to 178 to 1680 of the HUJ virus from the Master Virus Bank, that covers most of the F gene was found to be identical to the nucleotide sequence of the HUJ virus from the Master Virus Bank. This indicated that the identity of the 2) Fusion Activity Fusion activity was determined by chicken erythrocyte hemolysis as described in the literature (Nishikawa K et al 1986 J. Viral 60: 987–993). The results indicated that virus dilutions of 1:32–1:64 caused hemolysis, suggesting that fusion activity was similar for the two NDV strains.

3) Cytotoxic (Oncolytic) Effect

Cytotoxic Effect of NDV on Daudi Cells in Culture

Virus (20–200 $EID_{50}$/cell) was incubated with Daudi cells for different time intervals. At the end of the incubation, samples were checked for viability by staining with erythrosine B, a selective stain for dead cells (Hanks J H and Wallace J 1958 Proc Expel Biol Med 98 188).

A graphic presentation of the results is shown in FIG. 1.

The results indicate that the HUJ strain of NDV is similarly efficient in killing Daudi cells as the MTH strain.

Apoptosis of Daudi Cells following Treatment by NDV

Daudi cells were incubated in the presence of either MTH or HUJ strains (100 $EID_{50}$/cell) for the indicated time periods. Apoptosis was determined by a colorimetric assay using MTT tetrazolium (Mosmann T 1983, J of immunol. Methods 65: 55–63). MTT is a color reaction expressed by OD indicating apoptosis of cells. The intensity of OD measured at 570 nm correlate directly with cell viability. Higher OD indicates higher viability and lower % of dead cells.

Figure 2:
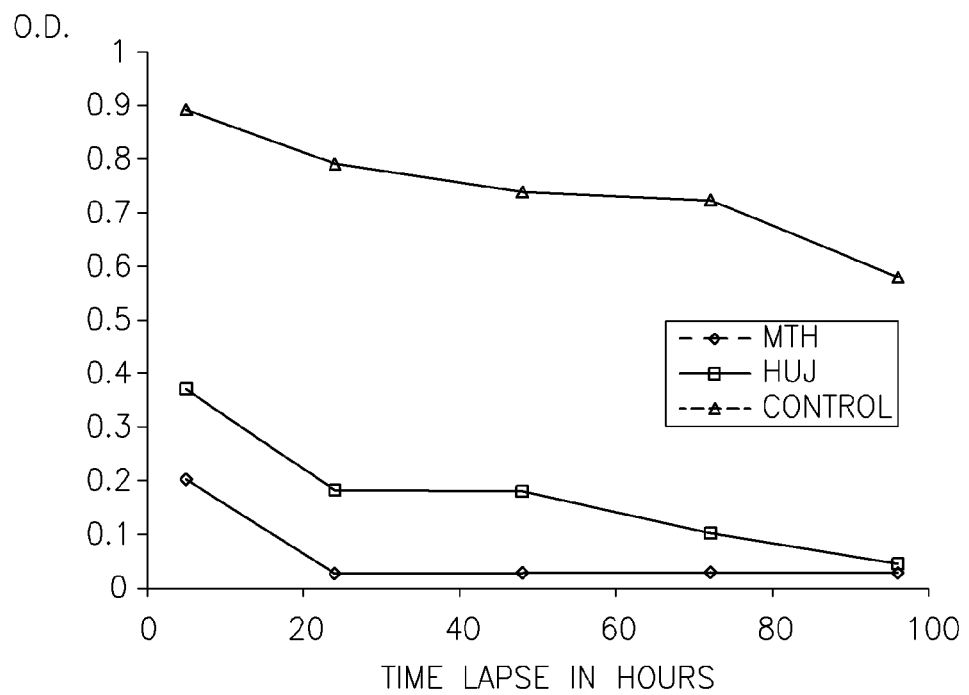
FIG. 2 is a graph showing apoptosis of Daudi cells in culture following interaction with two NDV strains (HUJ and MTH)

+A graphic presentation is shown in FIG. 2.

The effect of MTH strain on cytotoxicity (FIG. 1) and apoptosis (FIG. 2) is more rapid than that observed with the HUJ strain. However, after 96 hours of incubation both strains exhibit identical effect. Both viruses were also found to arrest cell replication. Previously, BarEli et al., showed the preferential effect of NDV on lymphoma cells when compared to non cancerous cells. It was also found that the NDV was not cytotoxic to normal human embryo fibroblasts.

The effectiveness of the HUJ strain in killing cells in culture was tested in the range of 20 $EID_{50}$/cell to 2000 $EID_{50}$/cell and was found to be effective in this range. Thus, treatment that includes locally administering HUJ NDV to a tumor (alone or as an active component in a composition) would preferably consist of estimating the number of cells in the tumor or estimating the size of a tumor and administering HUJ NDV strain in the range of 20 $EID_{50}$/cell to 2000 $EID_{50}$/cell, or an equivalent amount of surface glycoproteins, according to the invention. Systemic treatment of a patient would preferably consist of administering at least one dose of $10^6$–$10^{12}$ $EID_{50}$ of HUJ NDV strain or an equivalent amount of surface glycoproteins, according invention.

4) Thermostability of Hemagglutinin Activity at 56° C.

The hemagglutinin thermostability of the MTH and HUJ strains was determined at 56° C. using chicken erythrocytes according to the method of F. M. Burnet as described in "The affinity of Newcastle disease virus to the influenza virus group. Aust. J. Exp. Biol. Med 1942, 20, 320–328.

Figure 3A:
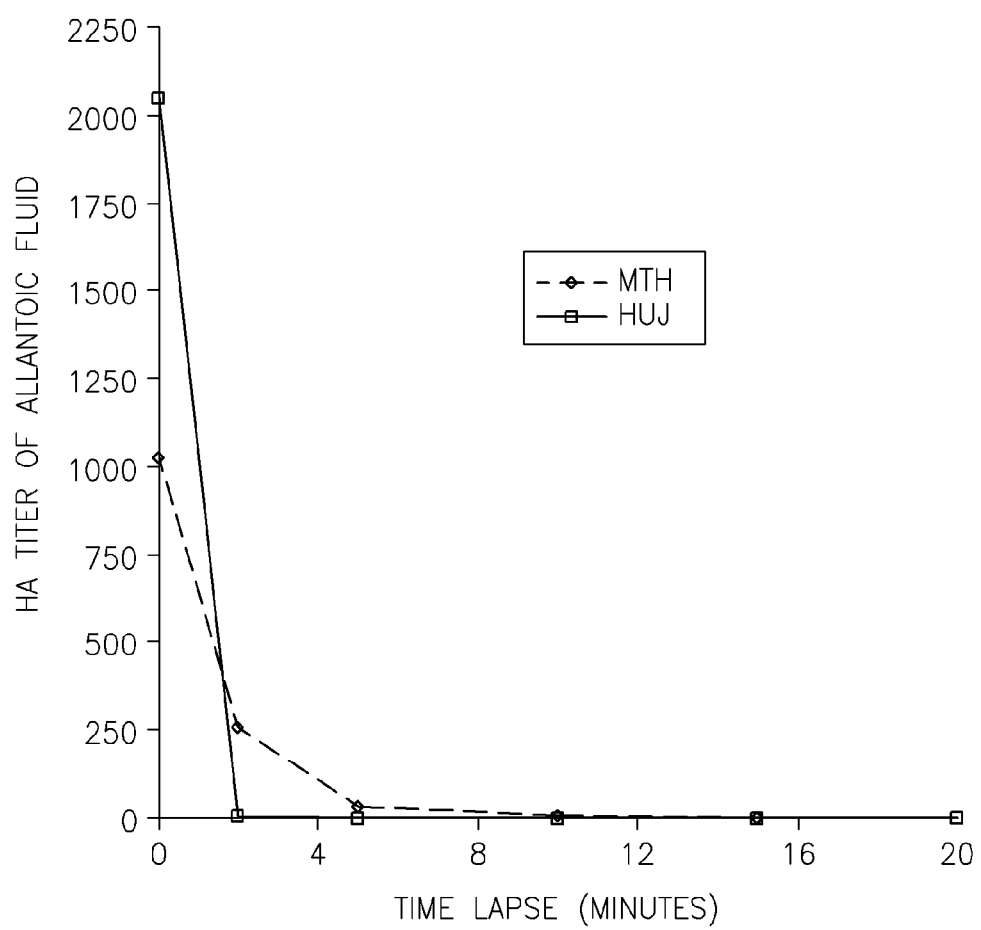
FIGS. 3A and 3B depict graphs showing thermostability of hemagglutinin activity at 56° C., for two NDV strains (HUJ and MTH) in two experiments.
Figure 3B:
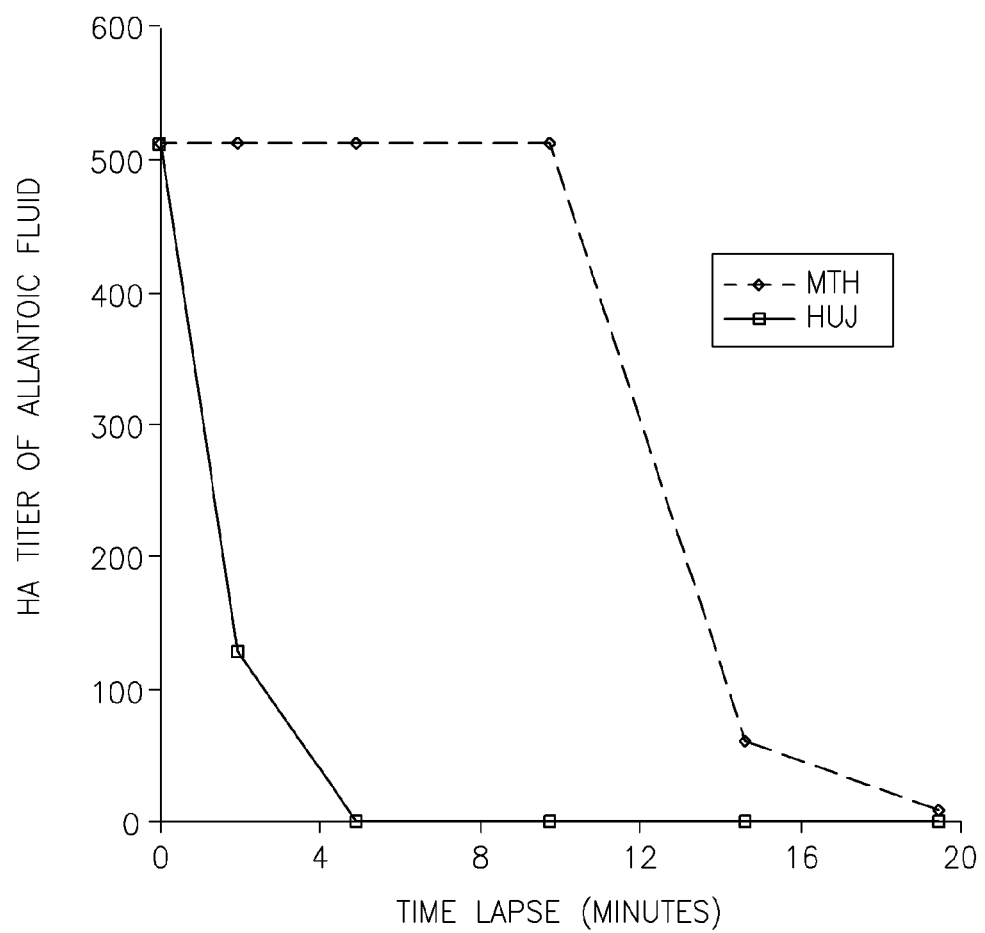
Figure 4:
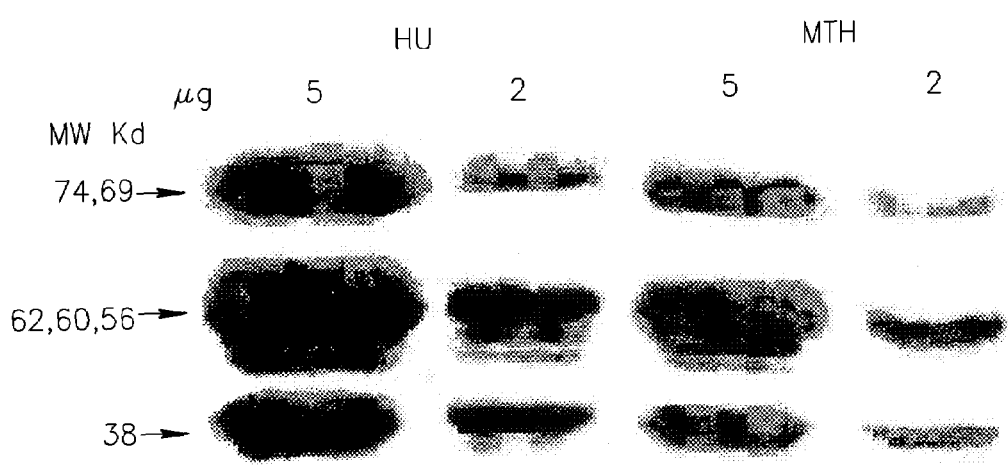
FIG. 4 is a picture of an SDS Polyacrylamide gel after electrophoresis of NDV virion proteins (strains HUJ and MTH)

The results are presented in FIGS. 3A and 3B and in Tables 3A and 3B.

TABLE 3A

| Time lapse | HA titer allantoic fluid | | HA titer purified fluid | |
|---|---|---|---|---|
| (minutes) | MTH | HUJ | MTH | HUJ |
| 0 | 1024 | 1024 | 1024 | 2048 |
| 2 | 256 | 8 | 256 | 0 |

TABLE 3A-continued

| Time lapse | HA titer allantoic fluid | | HA titer purified fluid | |
|---|---|---|---|---|
| (minutes) | MTH | HUJ | MTH | HUJ |
| 5 | 128 | 0 | 32 | 0 |
| 10 | 32 | 0 | 8 | 0 |
| 15 | 8 | 0 | 0 | 0 |
| 20 | 0 | 0 | 0 | 0 |
| 25 | 0 | 0 | 0 | 0 |
| 30 | 0 | 0 | 0 | 0 |

TABLE 3B

| Time lapse | HA titer allantoic fluid | | HA titer titer purified fluid | |
|---|---|---|---|---|
| (minutes) | MTH | HUJ | MTH | HUJ |
| 0 | 512 | 512 | 1024 | 2048 |
| 2 | 512 | 128 | 512 | 0 |
| 5 | 512 | 0 | 16 | 0 |
| 10 | 512 | 0 | 8 | 0 |
| 15 | 64 | 0 | 0 | 0 |
| 20 | 8 | 0 | 0 | 0 |

The results indicate that the hemagglutinin activity of the MTH strain is more thermostable since it is maintained for about 10 min at 56° C., while that of the HUJ strain is more labile since no activity is observed already after 2 min in both allantoic fluid and purified virus.

5) Sensitivity to Thermolabile β Inhibitors in Sera

NDV stains are known to be sensitive to the β inhibitors non-specific inhibitors in normal sera. Assays with horse sera that contain β inhibitors indicated that the HUJ strain is less sensitive to inhibitors than the MTH strain.

TABLE 4

| Titer of inhibitors* | | | | | | |
|---|---|---|---|---|---|---|
| HUJ | | | MTH | | | |
| Non-treated | 58° | RDE** | Non-treated | 58° | RDE | Horse sera |
| 10* | 10 | 10 | 160 | ND | ND | 1 |
| 10 | 10 | 10 | 320 | 160 | 40 | 2 |
| 10 | 10 | 10 | 80 | ND | ND | 3 |
| 2560 | 2560 | 1280 | 1280 | 2560 | 1280 | Rabbit immune |

*reciprocal titer
**RDE means receptor destroying enzyme

Pathogenicity of NDV Strains

6) Mean Death Time

The mean death time (MDT) of embryos indicates the virulence of the virus. The MDT was determined by the inoculation of SPF chicken eggs with serial dilutions of the cloned viruses using the method described in Manual of Standards for Diagnostic Tests and Vaccines, 4th edition, 2000. Death of embryos was determined in the different dilutions and the MDT (the mean death time of embryos infected with the highest dilution causing 100% death) was determined. The MDT of the original Hungarian MTH strain was shown to be less than 65 hours. The MDT of HUJ was >96 h, which is typical for lentogenic viruses. The MDT of chick embryos infected with virus from the virus working seed bank derived from the virus master seed bank was greater than 100 hrs. These results indicate that the original MTH strain is mesogenic, while the HUJ of the present invention is lentogenic.

7) Replication of Virus in Chicken Embryo Fibroblast Cultures (CEF) with and without Trypsin(Try)

TABLE 5

| MTH Titer ($TCID_{50}$) | | | | HUJ Titer ($TCID_{50}$) | | | |
|---|---|---|---|---|---|---|---|
| −Try | | +Try | | −Try | | +Try | |
| CPE | HA | CPE | HA | CPE | HA | CPE | HA |
| $10^{7.5}$ | $10^{8.5}$ | $10^{8.5}$ | $10^{8.5}$ | $10^{2.6}$ | $10^{2.5}$ | $10^{8.5}$ | $10^{5}$ |
| $10^{8.5}$ | $10^{5.5}$ | $10^{8.5}$ | $10^{8.0}$ | | | | |
| | $10^{9.5}$ | | $10^{9.5}$ | $10^{3.0}$ | $10^{3.0}$ | $10^{8.5}$ | $10^{6}$ |

Cloned virus with the same HA titer (1:200) was inoculated in serial dilutions into CEF monolayer cultures. Replication was followed by observation of CPE (cytopathic effect) and hemagglutination (HA) assay in the medium, and the titer tissue culture infectious dose 50% ($TCID_{50}$) was determined by the Reed and Muench method.

Replication of the virus without trypsin indicates elevated virulence. It may indicate that the amino acid residues at the trypsin cleavage sites of the surface glycoproteins are multi basic (arginine or lysine).

The MTH strain replicates to similar titers with or without trypsin, unlike the HUJ strain that replicates to a much higher level in the presence of trypsin ($10^{3.0} \rightarrow 10^{8.5}{}_{TCID50}$). This would clearly indicate that the MTH strain is more pathogenic than the HUJ virus, which probably has one basic amino acid residue at the cleavage site.

8) Serology

Most of the NDV strains are similar serologically. When using polyclonal rabbit anti NDV hyperimmune sera to the Israel mesogenic strain previously isolated by the inventors, both strains were similarly inhibited (H titer 1:1280) (see Table 6). However, human sera obtained from MTH—treated cancer patients had higher antibody titers to the homologous MTH strain than to the HUJ strain as shown in Table 6 rows I,II,III in the inhibition of hemolysis, hemagglutination and neuraminidase. Also, an immune rabbit serum that had similar HI antibody titer to both NDV strains, demonstrated different antibody titers to other viral activities (hemolysis and neuraminidase).

TABLE 6

| Serum | Inhibition of biological activities MTH | HUJ |
|---|---|---|
| Inhibition of hemolysis* | | |
| I Treated patients | | |
| 1 | 40–80* | 5–10 |
| 2 | 20–40 | 5–10 |
| Rabbit (Hyper immune serum) | 160 | 20 |
| **Hemagglutination inhibition*(HI)** | | |
| II Treated patients | | |
| 1 | 2560 | 1280 |
| 2 | 2560 | 640 |
| 3 | 320 | 20 |
| 4 Rabbit (Hyper immune serum) | 1280 | 1280 |
| Neuraminidase inhibition* | | |
| III Treated patients | | |
| 1 | 1280 | 640 |
| 2 | 2560 | 320 |
| 3 | 320 | 80 |

*reciprocal titers

The assays were conducted according to Sever Aymard-Henry and Nishikawa.

9) Neutralization in Eggs

Sera from cancer patients treated with MTH was interacted with 100 $EID_{50}$ of each of the two NDV strains. The m was then inoculated into 10–11-day-old embryos. 48 hours later, neutralization of the virus was determined by hemagglutination assay. Also neutralizing antibody level was higher against the homologous strain (in this case the MTH Neutralizing serum titer was 1:320 against MTH and only 1:20 against HUJ (serum 1). Neutralizing serum titer was 1:320 to MTH and only 1:80 for HUJ (serum 2).

Analysis of NDV HUJ Strain Proteins

In order to compare proteins of the two NDV strains MTH and HUJ, purified virion preparations (See NDV Preparation and Purification, above) were treated with SDS and the denatured proteins were analyzed by electrophoresis in a 10% SDS Polyacrylamide gel. A picture of the SDS Polyacrylamide gel analysis of NDV virion proteins is shown in FIG. 4. Electrophoresis in Polyacrylamide gel (10%) of the MTH and HUJ proteins was carried out with 2 μg and 5 μg viral proteins and the gel was subsequently stained with Coommassie blue (Millar N S et al., (1988). *J. Gen. Virol.* 69 (3), 613–20).

As observed in FIG. 4, six major proteins were resolved in the gel. These six proteins correspond to the known major structural proteins of NDV, P-69 kD; HN-74 kD; F0-62kD; F-56kD; NP-60kD and M-38kD (Hightower, L. E., Morrison, T. B. and Bratt M. A. (1975) *J. Virol* 16, 1599–1607). No differences in the apparent molecular weights of the major virion proteins of strains MTH and HUJ could be observed by this method.

NDV Surface Glycoproteins

Cytotoxicity of NDV Surface Glycoproteins

Adsorption of Newcastle Disease Virus surface glycoproteins to Daudi cells, without subsequent penetration, caused a rapid inhibition in cellular DNA synthesis, arrest in cell multiplication and eventually killing of the cells. Surface glycoproteins obtained from a mesogenic strain (Roakin) were more effective than those originating from a lentogenic strain (B-1).

Thus, it appeared that adsorbed glycoproteins distorted the integrity of the cell membrane, increasing its permeability, as was indicated by the elevation in $^{51}Cr$ release. The killing of the cells may presumably be linked to a specific cytopathic effect through signal transduction, mediated by the exogenous viral glycoproteins.

The strains used in these experiments are the lentogenic B-1 strain (B1) and the mesogenic Roakin/46 V NJ stain (RO) obtained from the American type collection 1971.

Production of Viral Surface Glycoproteins:

For the solubilization of hydrophobic membrane proteins, purified virus preparations were treated with a non-ionic detergent NP40 (Sigma), 0.2% for 30 min at 4° C. The detergent was extracted five times with a 1:1 volume of analytical ether (May and Baker Ltd., England). The ether was then evaporated by nitrogen. Viral core was removed by high-speed centrifugation (L-2 rotor Ti50) at 20,000 rpm for 45 min at 4° C. The surface glycoproteins in the supernatant were kept at −70° C. A buffer solution was subjected to an identical treatment and served for control purposes to assure that any effect would not be due to residual detergent It will be appreciated by persons skilled in the art that surface glycoproteins can be obtained by several other known methods and using other detergents.

Biological Activities of NDV Surface Glycoproteins

The fraction obtained by treatment with NP-40 contained the surface glycoproteins Hemagglutinin-Neuraminidase (NH) and Fusion (F). In Table 7 (below) the biological properties of the glycoprotein fractions originating from a mesogenic (RH) and a lentogenic (BHN) strain, are depicted. The infectivity of the two purified virus preparations from which the surface glycoproteins were extracted was $10^{9.3}$ $EID_{50}/0.2$ ml. No infectivity was recorded in the soluble fraction containing the surface glycoproteins obtained from Roakin or B-1 strains, RHN and BHN, respectively. Protein concentration (μg/ml) was similar in the two virus suspensions before extraction. After extraction, similar protein concentration, although lower as expected, was obtained in the two surface glycoprotein fractions of the two strains.

Hemagglutination activity of the surface glycoproteins fraction was similar to the original whole virus preparation. Neuraminidase activity, however, declined to 33 and 50% of the full value of intact virus suspension in Roakin and B-1 glycoproteins fractions, respectively. Hemolytic activity was high in the intact virus preparations while only a small portion of this activity (6%) was retained in the isolated surface glycoprotein fractions.

TABLE 7

Activities of intact virus and surface glycoprotein preparations.

| Preparation | Infectivity* $EID50/$ 0.2 ml | HA** ×10³ | NA+ | Hemolysis++ | Proteins# μg/ml |
|---|---|---|---|---|---|
| RO | $10^{9.3}$ | 30 | 480 | 1.73 | 480 |
| RHN | <1 | 29 | 160 | 0.09 | 165 |
| B-1 | $10^{9.3}$ | 39 | 640 | 1.81 | 470 |
| BHN | <1 | 32 | 320 | 0.12 | 158 |

*Viral infectivity, calculated as median egg-infective dose/0.2 ml according to Reed and Muench.
**The reciprocal of the highest dilution that agglutinate CRBC
+The reciprocal of the highest dilution with enzyme activity (OD 540 nm)
++Absorbency of the supernatant of CRBC treated with water (100% hemolysis) was measured at OD 540 nm.
Determined by the Lowry method.

Cytotoxic Effect of NDV Surface Glycoproteins on Daudi Cells

Adsorption of RHN and B-HN virus to Daudi cells was monitored by an indirect immunofluorescence using diluted virus specific antiserum (chicken or rabbit) and fluorescein-conjugated goat anti chicken or anti rabbit IgG. Over 90% of the cells demonstrated intensive staining 60 minutes after virus interaction The number of the viable and dead Daudi cells after incubation with the different viral preparations was determined at different periods of time (in hours FIGS. 5A and 5B).

Cell multiplication as measured by the total number of viable cells was completely inhibited, and after 72 hr all the cells were dead following interaction with whole virus preparations (RO, B-1), which were used as control and reference for the destructive capability of the surface glycoproteins. In another experiment, RHN fraction inhibited cell multiplication at a slower rate and over 70% of the cells were damaged and destroyed.

Figure 5A:
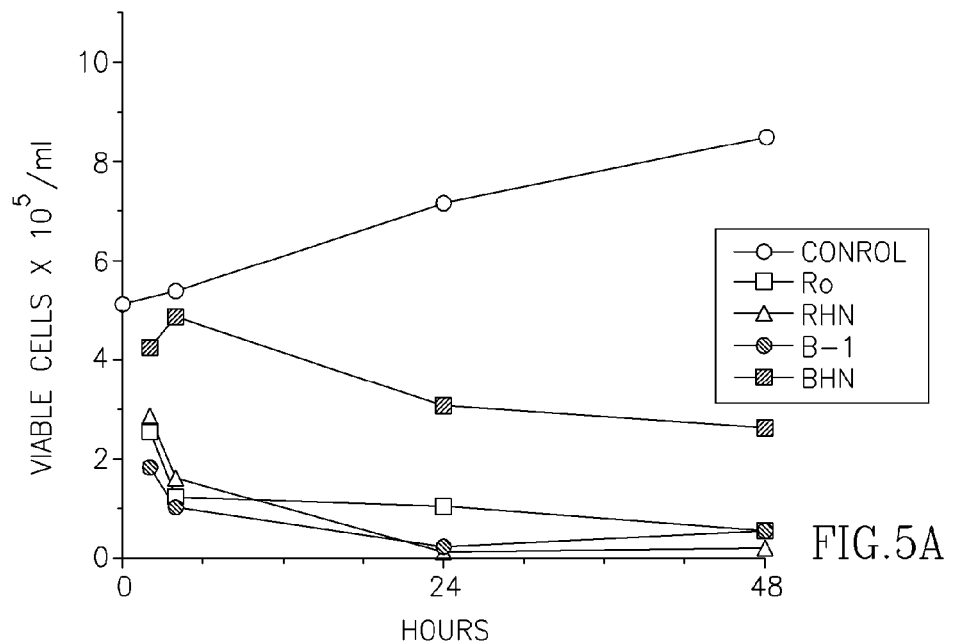
FIG. 5A and 5B show graphs of viability and mortality of Daudi cells after incubation with NDV strains (Roakin and B-1) or with surface glycoproteins (RHN and BHN) extracted from these stains.
Figure 5B:
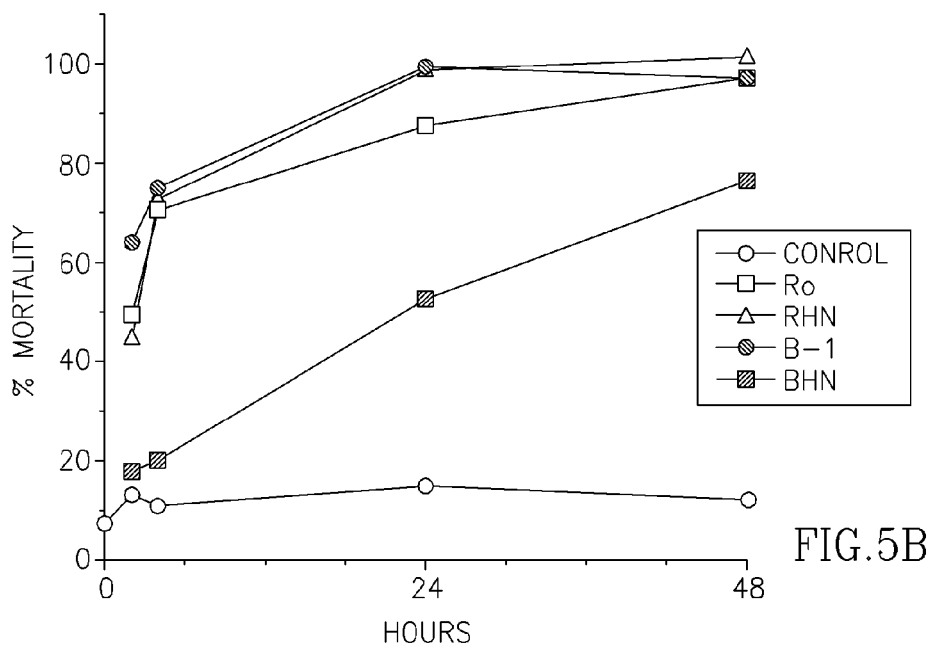

BHN fraction, on the other hand, displayed different levels of activity on individual isolates of target cancer cells. Thus the BHN fraction was comparatively ineffective on Daudi D-1 cell isolate and the percentage of death was similar to control cells. However, when an additional isolate of Daudi cells was used (D2) it exhibited a very high sensitivity, 100% of cells were killed by RHN fraction and 74% by the BHN fraction within 72 h (FIGS. 5A and 5B). The subsequent experiments were carried out with the D-2 line.

DNA Synthesis

Figure 6:
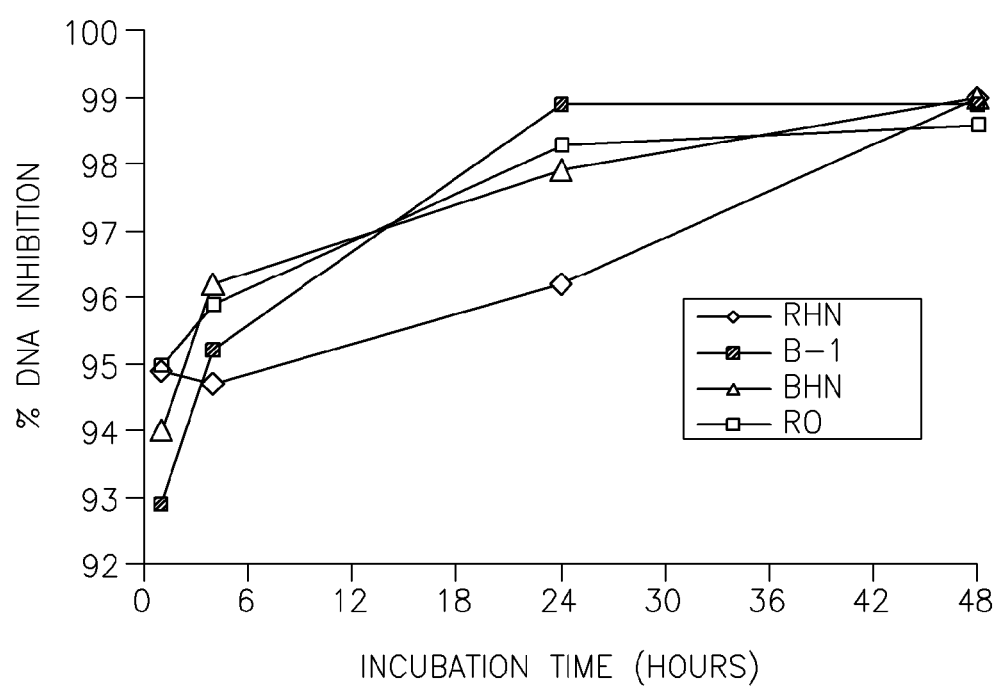
FIG. 6 depicts a graph showing the inhibition of cellular DNA synthesis in Daudi cells (D-2) in response to their incubation in the presence of NDV strains (Roakin and B-1) or in the presence of the surface glycoproteins (RHN and BHN) extracted from these strains.
Figure 7:
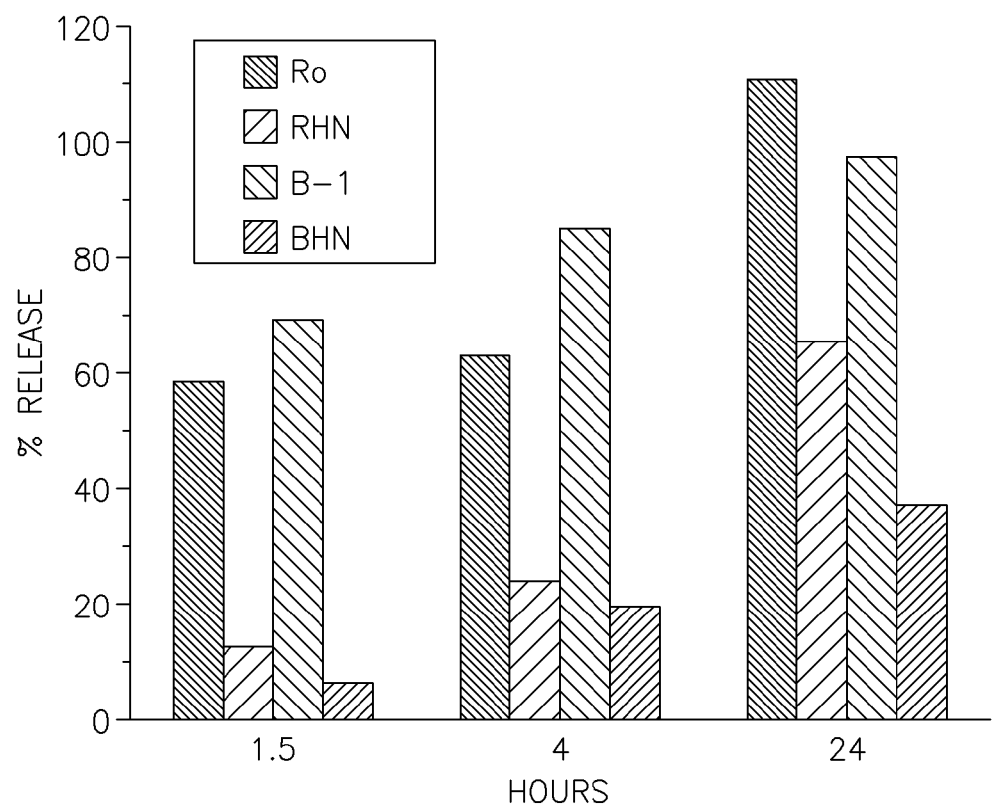
FIG. 7 depicts the $Cr^{51}$ release from NDV infected cells.

A rapid inhibition of DNA synthesis (90–95%) was observed after 1 h of interaction of cells with NDV strains and fractions RO, RHN, B-1 and BHN. This inhibition was maintained throughout the experiment and reached 99% inhibition at 48 h (the results are shown in FIG. 6 and in Table 7 below).

TABLE 8

Inhibition of cellular DNA synthesis

| Incubation (D-2) | % DNA inhibition NDV strain/fraction | | | |
|---|---|---|---|---|
| (hours) | RO | RHN | B-1 | BHN |
| 1 | 95 | 94.9 | 92.9 | 94 |
| 4 | 95.9 | 94.7 | 95.2 | 96.2 |
| 24 | 98.3 | 96.2 | 98.9 | 97.9 |
| 48 | 98.6 | 99 | 98.9 | 99 |

The inhibitory effect is NDV virus specific, as pretreatment of viral preparations (intact virus or isolated surface glycoproteins) with specific antiserum abolished cytotoxicity.

Elevation in Cell Membrane Permeability

Cells were labeled with $^{51}Cr$ and interacted with the different NDV preparations. Following different time intervals radioactive leakage was determined in comparison with spontaneous release from uninfected control Daudi cells. As shown in FIG. 8, a significant $^{51}Cr$ release was already observed 90 minutes following interaction with NDV RO (59%) and B-1 (79%), while only a low percentage of release was caused by RHN (12%) and BHN (6%).

The release was elevated further to 60, 85, 23, and 18% at 4 h post interaction with RO, B-1, RHN and BHN, respectively. At 24 h a total release (100%) resulted from the interaction with the intact virions, 65% release was recorded as a result of interaction with RHN and only 36% release was found in cells interacted with BHN. In cells interacting with control fluids, or in uninfected cells, no elevation in membrane permeability and no cell damages was observed.

Tissue Culture

Effect of Virus Cultivated in Cultured Primary Chicken Fibroblasts (CF)

Figure 8A:
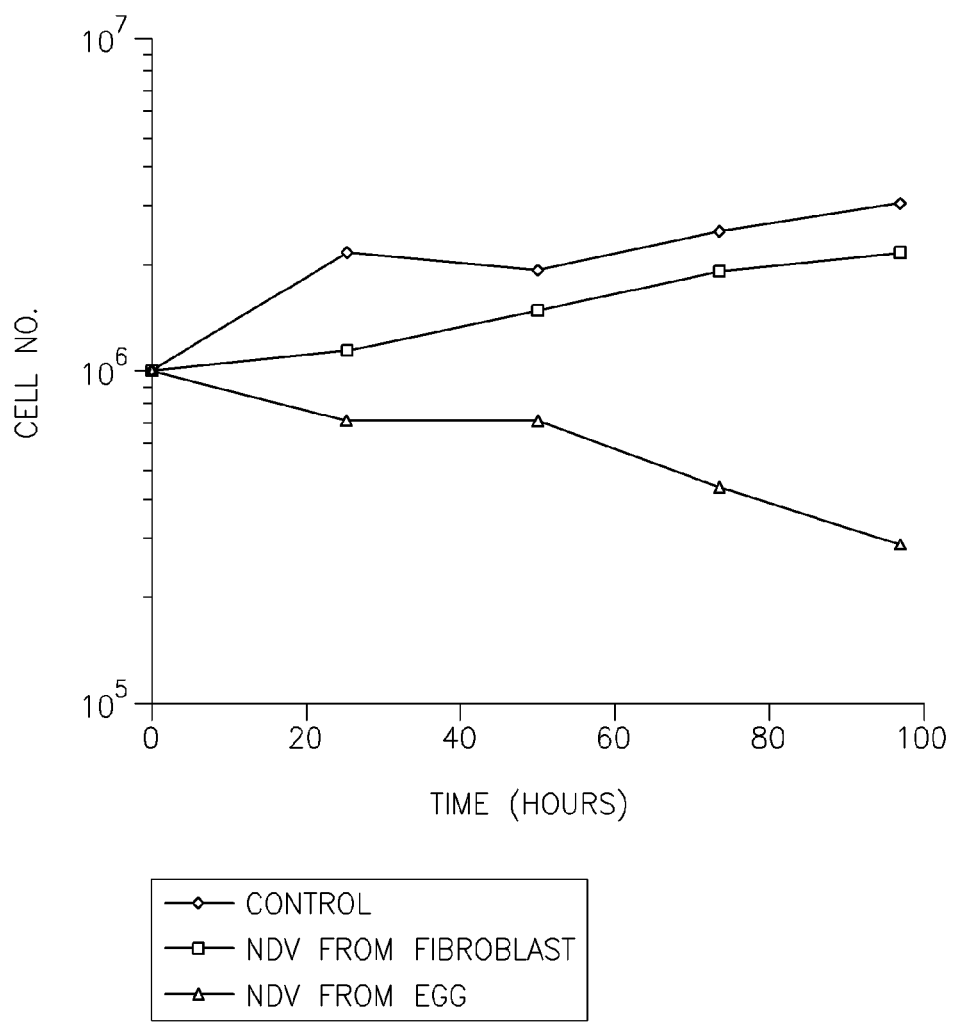
FIGS. 8A, B and C depict graphs showing the effect of NDV propagated in tissue culture or in embryonated eggs on Daudi cells: the effect on the total number of cells (FIG. 8A), percentage of dead cells following infection (FIG. 5B) and, the effect of treatment with trypsin on the cytotoxic activity of the NDV (FIG. 8C)
Figure 8B:
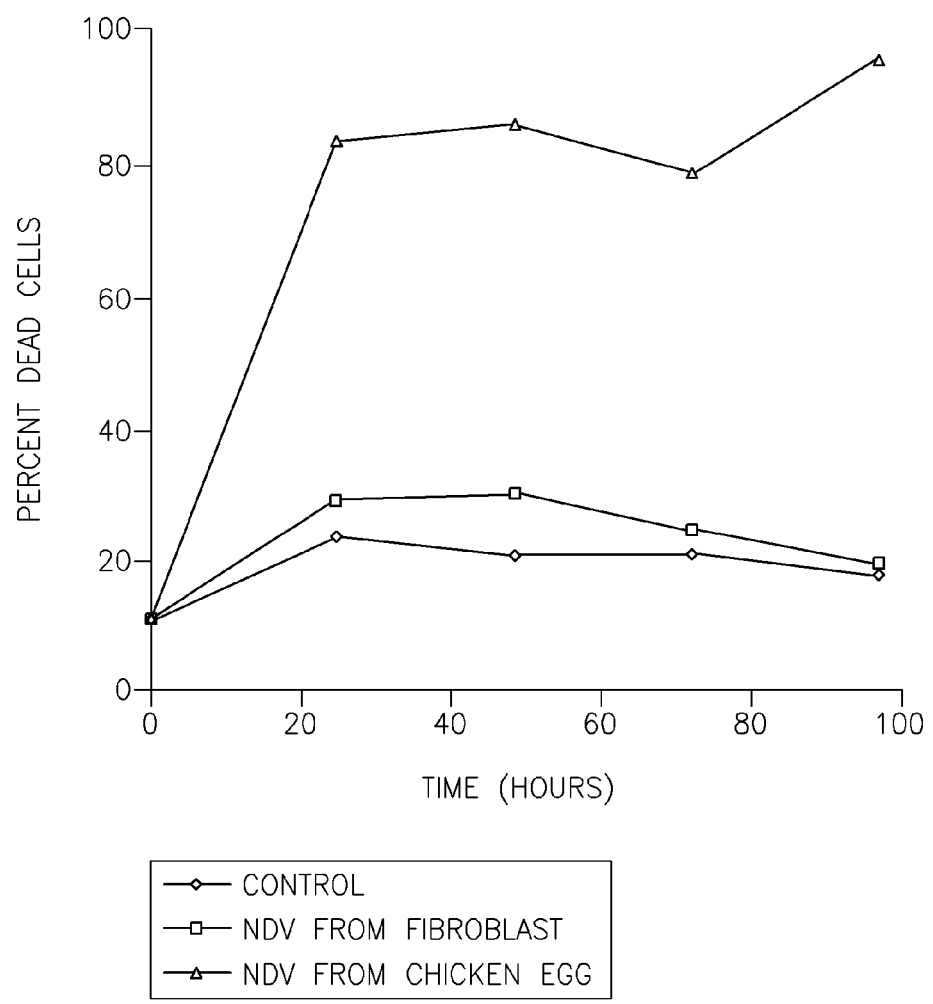
Figure 8C:
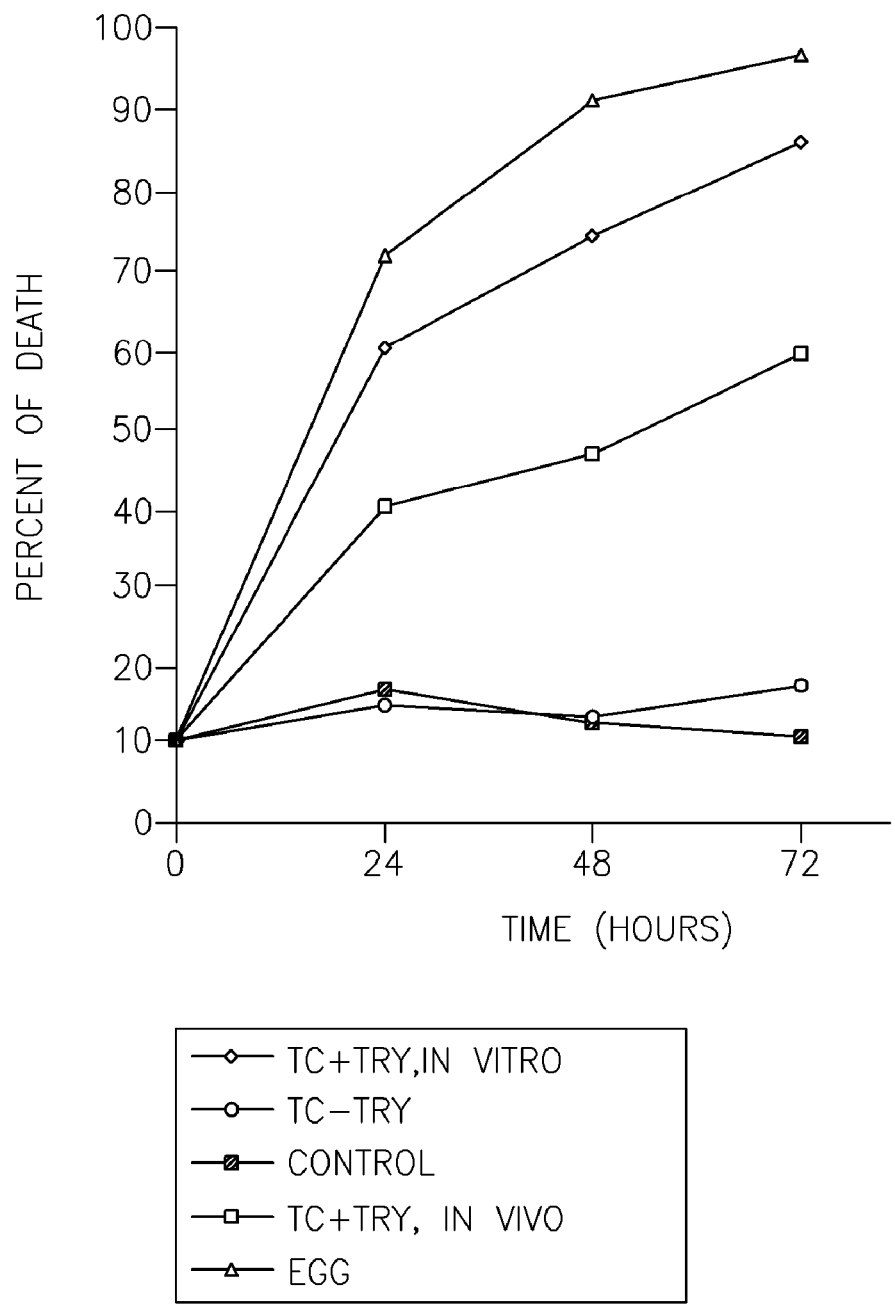

The cytotoxic effect of NDV strains on Burkitt lymphoma Daudi cells was studied. Interaction of cells with mesogenic (Roakin), as well as of active attenuated lentogenic strain (B-1) cultivated in the allantoic sac of embryonated eggs, lead to cell death (90%). However, lentogenic strains cultivated in chicken fibroblasts (CF) exhibited a very low activity with only 10% cell death (FIGS. 8A–C). The activity was found to be dependent on the cleavage of the viral surface glycoproteins (Hemagglutinin Neuraminidase (HN) and Fusion (F)).

While the glycoproteins of both the mesogenic and the lentogenic strains undergo cleavage by the proteases in the embryonated eggs, the lentogenic strain that has one glutamine residue in the cleavage site of F0 and of HN0, is insensitive to the proteases of the CF. Cultivation of the virus in CF, in the presence of trypsin (CFT), or treatment of the purified virus preparation with trypsin (NDVT) restored virus activity as detected by cell death (66% and 93% cell death, respectively). Neuraminidase and hemagglutinin activities are similar in treated and non-treated virus preparation as demonstrated by a hemagglutination test, viral adsorption on cells using fluorescent staining and a neuraminidase assay.

Figure 9:
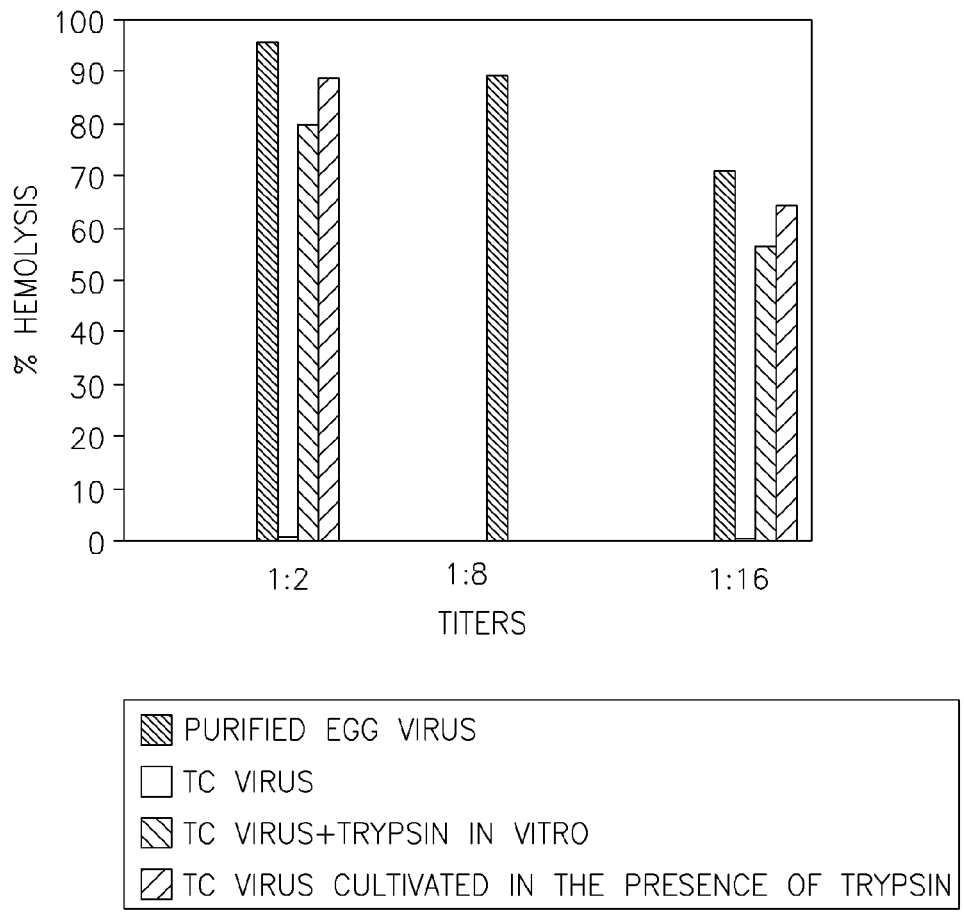
FIG. 9 shows a histogram of the F glycoprotein activity as indicated by hemolysis of erythrocytes.

The fusion glycoprotein of the CF grown virus is almost completely inactive, as indicated by lack of hemolysis of red blood cells (in 1:2 dilution only 31% hemolysis was recorded in comparison to 71% hemolysis in 1:32 dilution of egg grown virus). Trypsin elevated activity to 58% and 64% hemolysis in 1:16 dilution of CFT and NDVT, respectively (Tables 9, and 4 and FIG. 9).

It seems, therefore, that the fusion glycoprotein which is responsible for the fusion of cell virus membranes plays a crucial role in the cytotoxic effect of the virus.

TABLE 9

Activity of F glycoproteins (virus)

| | titer | % hemolysis | titer | % hemolysis | titer | % hemolysis |
|---|---|---|---|---|---|---|
| Purified egg | (1:2) | 95.4 | (1:8) | 89.4 | (1:16) | 71 |
| CF | (1:2) | 0.3 | | | | |
| CF + trypsin | (1:2) | 80 | | | (1:16) | 58 |
| In vitro Cultivated in CF + trypsin | (1:2) | 88.8 | | | (1:16) | 64 |

It will be appreciated by persons skilled in the art that the present invention is not limited by what has been particularly shown and described herein above. Rather the scope of the invention is defined by the claims which follow.

---

The invention claimed is:

1. An isolated lentogenic oncolytic strain of Newcastle Disease Virus (NDV) comprising the DNA nucleotide sequence of SEQ ID NO: 1 encoding for the fusion (F) gene and at least part of the hemaglutinin-neuraminidase (HN) gene.

2. A pharmaceutical composition for the treatment of cancer comprising the clonal lentogenic oncolytic strain of Newcastle Disease Virus (NDV) according to claim 1, optionally in combination with a suitable carrier.

3. The pharmaceutical composition according to claim 2 wherein the carrier is present.

4. The pharmaceutical composition according to claim 2 wherein the strain is present in an amount of $10^6$–$10^{12}$ $EID_{50}$ per unit dose.

5. A method for treating cancer in a patient comprising administering to the patient in need thereof a therapeutically effective amount of a pharmaceutical composition according to claim 3.

6. The method of claim 5 wherein the step of administering is selected from intravenous, oral, buccal, intranasal, inhalation, topical application to a mucosal membrane or injection, including intradermal, intrathecal, intracisternal, and intralesional injection.

7. The method of claim 5 wherein the step of administering comprises locally administering the composition to a tumor or in its vicinity.

8. The method of claim 5 wherein the strain is present in the composition in an amount of $10^6$–$10^{12}$ $EID_{50}$ per unit dose.

9. The method of claim 5 wherein the step of administering comprises administering the HUJ strain of NDV in a range of 20 $EID_{50}$/cell to 2000 $EID_{50}$/cell.

10. A method of making the pharmaceutical composition according to claim 3, which comprises incorporating in the composition the clonal lentogenic oncolytic strain of Newcastle Disease Virus (NDV) comprising the DNA nucleotide sequence of SEQ ID NO: 1 encoding for the fusion (F) gene and at least part of the hemaglutinin-neuraminidase (HN).

* * * * *

UNITED STATES PATENT AND TRADEMARK OFFICE
CERTIFICATE OF CORRECTION

PATENT NO.        : 7,223,389 B2                                                Page 1 of 1
APPLICATION NO.   : 10/800256
DATED             : May 29, 2007
INVENTOR(S)       : Zakay-Rones et al.

It is certified that error appears in the above-identified patent and that said Letters Patent is hereby corrected as shown below:

Column 39:
Line 45, after "An isolated", insert -- clonal --.
Line 65, after "to claim", delete "3" and insert -- 2 --.

Column 40:
Line 60, after "according to claim", delete "3" and insert -- 2 --.

Signed and Sealed this

Tenth Day of July, 2007

JON W. DUDAS
*Director of the United States Patent and Trademark Office*